(12) United States Patent
Yeh

(10) Patent No.: US 11,744,951 B2
(45) Date of Patent: Sep. 5, 2023

(54) SYRINGE WITH INJECTION DOSE ADJUSTMENT FUNCTION

(71) Applicant: CC Biotechnology Corporation, Tainan (TW)

(72) Inventor: Chin-Min Yeh, Tainan (TW)

(73) Assignee: CC BIOTECHNOLOGY CORPORATION, Tainan (TW)

( * ) Notice: Subject to any disclaimer, the term of this patent is extended or adjusted under 35 U.S.C. 154(b) by 318 days.

(21) Appl. No.: 17/287,035

(22) PCT Filed: Oct. 24, 2018

(86) PCT No.: PCT/CN2018/111608
§ 371 (c)(1),
(2) Date: Apr. 20, 2021

(87) PCT Pub. No.: WO2020/082260
PCT Pub. Date: Apr. 30, 2020

(65) Prior Publication Data
US 2021/0379284 A1 Dec. 9, 2021

(51) Int. Cl.
*A61M 5/315* (2006.01)
*A61M 5/24* (2006.01)
*A61M 5/31* (2006.01)

(52) U.S. Cl.
CPC ...... *A61M 5/31528* (2013.01); *A61M 5/2422* (2013.01); *A61M 5/3155* (2013.01);
(Continued)

(58) Field of Classification Search
CPC .. A61M 2005/2403; A61M 2005/2407; A61M 2005/2411; A61M 2005/2414; A61M 2005/2488; A61M 2005/2492; A61M 2005/2496; A61M 2005/3125; A61M 2005/3126; A61M 2005/31508; A61M 5/24; A61M 5/2422; A61M 5/315;
(Continued)

(56) References Cited

U.S. PATENT DOCUMENTS

| 6,666,849 | B1 | 12/2003 | Marshall et al. |
| 2011/0313396 | A1 | 12/2011 | Chanoch et al. |
| 2017/0239424 | A1 | 8/2017 | Wei |

FOREIGN PATENT DOCUMENTS

| CN | 203090111 U | 7/2013 |
| CN | 103260674 A | 8/2013 |

(Continued)

*Primary Examiner* — Shefali D Patel
(74) *Attorney, Agent, or Firm* — BACON&THOMAS,PLLC

(57) ABSTRACT

A syringe with an injection dose adjustment function, the syringe comprising a medicine vial connecting apparatus and an adjustable propulsion apparatus; by means of assembling the medicine vial connecting apparatus and a medicine vial, and then installing the adjustable propulsion apparatus in the medicine vial connecting apparatus and extending the adjustable propulsion apparatus into the medicine vial, a rotating knob of the medicine vial connecting apparatus can drive a push rod of the adjustable propulsion apparatus to move backward to a predetermined scale; at a time of injection, pressing the push rod enables the medicine vial to output a predetermined dosage of medicinal liquid, such that the syringe can adjust the dosage of the injection according to requirements of different injection subjects.

20 Claims, 17 Drawing Sheets

(52) U.S. Cl.
CPC ............. *A61M 2005/2411* (2013.01); *A61M 2005/2414* (2013.01); *A61M 2005/3126* (2013.01)

(58) Field of Classification Search
CPC .......... A61M 5/31501; A61M 5/31528; A61M 5/31533; A61M 5/31545; A61M 5/31548; A61M 5/3155; A61M 5/31551; A61M 5/31553; A61M 5/31565; A61M 5/31576; A61M 5/31578; A61M 5/3158; A61M 5/3159; A61M 5/31593
See application file for complete search history.

(56) References Cited

FOREIGN PATENT DOCUMENTS

| | | |
|---|---|---|
| CN | 103702700 A | 4/2014 |
| CN | 105813669 A | 7/2016 |
| TW | 201716092 A | 5/2017 |

SYRINGE WITH INJECTION DOSE ADJUSTMENT FUNCTION

CROSS-REFERENCE TO RELATED INVENTIONS

This patent invention is a national stage entry under 35 U.S.C. 371 and claims the benefit of International Appl. No. PCT/CN2018/111608, filed on Oct. 24, 2018, the entire contents of which are hereby incorporated herein by reference thereto.

BACKGROUND OF THE INVENTION

1. Field of the Invention

The present invention relates to a syringe, and especially a syringe that can be combined with a medicine vial containing a liquid medicine and has a function of adjusting an injection dose.

2. Description of Related Art

Based on the safety regulations for medicament liquid injection, the conventional syringes already have metered injection functions. That is, the metering type syringe is attached to a medicine vial. It uses a push rod at a back of the syringe to push a piston in the medicine vial to move a certain distance through a linkage control of an internal driving mechanism, and then output a predetermined dose of medicament liquid through a needle.

Although the aforementioned metered syringe can provide the function of outputting a fixed dose of medicament liquid, the injection dose usually needs to be adjusted according to the needs of different injection objects during the use of the syringe. The conventional metered syringe lacks the function of adjusting the injection dose, and it is difficult to meet the needs of different users.

SUMMARY OF THE INVENTION

The technical problem to be solved by the present invention is to provide a syringe with an injection dose adjustment function to solve the problem that the conventional syringe cannot adjust the injection dose according to the needs of different injection objects.

The technical solution proposed by the present invention is to provide a syringe with an injection dose adjustment function, which is characterized by including a medicine vial connecting apparatus and an adjustable propulsion apparatus; wherein:

the medicine vial connecting apparatus includes:

a housing, comprising a housing base, a medicine vial assembly portion, and a joining pipe portion, the medicine vial assembly portion and the joining pipe portion respectively formed on a front end and a rear end of the housing base, the housing having a housing middle hole extending from a front end to a rear end thereof, the medicine vial assembly portion having an assembly groove laterally formed therein and communicating with the housing middle hole;

a rotating knob, unidirectionally rotatably assembled on an outer side of the joining pipe portion of the housing, the rotating knob comprising a knob shell, a knob inner plate, a knob inner tube, and an inner hole, the knob inner plate formed in the knob shell, the knob inner tube disposed in the knob shell, the knob inner tube connected to a front end of the knob inner plate, and the inner hole disposed in the knob inner tube and the knob inner plate; and a zeroing nut base, connected to a shell rear section of the rotating knob, the zeroing nut base comprising a base mount, an assembly end portion, an assembly tube portion, and a nut inner tube, the assembly end portion and the assembly tube portion respectively formed on a front end and a rear end of the base mount, and the zeroing nut base having an inner shaft hole; and the adjustable propulsion apparatus is assembled in the medicine vial connecting apparatus, and the adjustable propulsion apparatus comprises:

a screw rod, comprising a screw body and a rubber stopper connecting portion formed on a front end of the screw body, the screw body having multiple screwing units formed on an outer peripheral surface thereof, the multiple screwing units equally spaced along an axial direction of the screw body, an annular slot formed between each two adjacent said screwing units, each screwing unit having a spiral groove, and a front end and a rear end of the spiral groove of each screwing unit respectively connected to the annular slots at a front position and a rear position of the screwing unit; and a push rod, the push rod assembled in the zeroing nut base, the push rod being linearly moveable relative to the zeroing nut base, the push rod rotated with the zeroing nut base, the push rod having a push rod hole formed therein, a scale formed on an outer peripheral surface thereof, and a threaded portion formed on an inner wall of the push rod hole, the screw rod assembled in the push rod hole of the push rod, the threaded portion of the push rod threaded with the spiral grooves of the screw rod, the screw rod being rotatable and moveable back and forth in the push rod, the push rod having a push arm, a front end of the push arm being a free end, and the push arm extending into the annular slot of the screw rod and pressed against an end surface of the screwing unit.

According to the above-mentioned syringe with an injection dose adjustment function, the housing has two unidirectional snap hooks formed on an outer side of the joining pipe portion at a rear side of the housing base, the rotating knob has two unidirectional buckle grooves formed on an inner peripheral wall of a shell front section of the knob shell, and the two unidirectional snap hooks selectively and respectively engage with the two unidirectional buckle grooves.

According to the above-mentioned syringe with an injection dose adjustment function, the zeroing nut base has at least one guide groove portion formed on an inner wall of the inner shaft hole, the push rod has a guide rail portion formed on the outer peripheral surface thereof and extending axially, the guide rail portion corresponds to the guide groove portion in the zeroing nut base, the push rod is linearly moveable relative to the zeroing nut base, and the push rod is rotatable together with the zeroing nut base.

According to the above-mentioned syringe with an injection dose adjustment function, the screw rod has a stop portion formed on the screw rod between the rubber stopper connecting portion and the screw body, and the stop portion of the screw rod limits a positon of the screw rod at a front end of the push rod.

According to the above-mentioned syringe with an injection dose adjustment function, the zeroing nut base has a guide groove portion formed on an inner wall of the inner shaft hole, the push rod has a guide rail portion formed on the outer peripheral surface thereof and extending axially, the guide rail portion corresponds to the guide groove portion in the zeroing nut base, the push rod is linearly moveable relative to the zeroing nut base, and the push rod is rotatable together with the zeroing nut base.

According to the above-mentioned syringe with an injection dose adjustment function, the knob shell of the rotating knob has an engaging portion formed on an inner peripheral wall thereof relative to a back of the knob inner plate; the assembly end portion has a pivot annular groove and an engaging annular groove formed on an outer peripheral surface of the assembly end portion at a spaced interval, the assembly tube portion has a screw thread formed on an outer peripheral surface thereof, the nut inner tube is disposed in the assembly end portion and extends forward from the base mount, the nut inner tube has a second locking portion formed on a front end thereof, the second locking portion has multiple locking recesses, the assembly end portion of the zeroing nut base is assembled in the shell rear section of the rotating knob, the engaging portion of the rotating knob is selectively engaged with the pivot annular groove or the engaging annular groove, and the second locking portion at the front end of the nut inner tube of the zeroing nut base is engaged with the first locking portion at the rear end surface of the knob inner plate of the rotating knob by concave-convex cooperation in a locked state; the medicine vial connecting apparatus further has a zeroing nut and a nut fixing piece, wherein: the zeroing nut has a screw hole formed therein, the zeroing nut has a threaded strip formed on an inner wall of the screw hole, the threaded strip has a vacant portion formed thereon, the zeroing nut has a pivot hole formed on a peripheral wall thereof, and a position of the pivot hole corresponds to that of the vacant portion. The zeroing nut has a first engaging segment formed on a rear end thereof, the zeroing nut is disposed on an outer side of the assembly tube portion of the zeroing nut base, and the threaded strip is screwed to the screw thread; the nut fixing piece includes a sheet, a pivot, and a protruding portion, the pivot is disposed on an end side of the sheet, the protruding portion is disposed on the pivot opposite to the sheet, the nut fixing piece is pivotally mounted in the pivot hole of the zeroing nut by the pivot, the sheet is located on an outer side of the zeroing nut, the protruding portion is located in the vacant portion of the threaded strip of the zeroing nut, the nut fixing piece is rotatable relative to the zeroing nut to change position relative to the vacant portion of the threaded strip; the adjustable propulsion apparatus has a bottom gear disk disposed on a rear end of the push rod, the bottom gear disk has a second engaging segment formed on a front side thereof, and the second engaging segment selectively engages with the first engaging segment at the rear end of the zeroing nut.

According to the above-mentioned syringe with an injection dose adjustment function, the adjustable propulsion apparatus has a bottom gear disk disposed on a rear end of the push rod, the bottom gear disk has a second engaging segment formed on a front side thereof, and the second engaging segment selectively engages with the first engaging segment at the rear end of the zeroing nut.

According to the above-mentioned syringe with an injection dose adjustment function, the housing has an indicator mark formed on an outer peripheral surface of the housing base, the rotating knob has a marking line formed on an outer peripheral surface of the knob shell, and the marking line aligns with the indicator mark of the housing.

According to the above-mentioned syringe with an injection dose adjustment function, the zeroing nut base has a rotation indicator formed on an outer peripheral surface thereof to indicate a direction of rotation.

The beneficial effect that can be achieved by the present invention is that the syringe with an injection dose adjustment function mainly utilizes a combined structure of the medicine vial connecting apparatus and the adjustable propulsion apparatus, and the medicine vial connecting apparatus is assembled to the medicine vial and then installed in the adjustable propulsion apparatus. That is, the rotating knob of the medicine vial connecting apparatus can be used to drive the push rod of the adjustable propulsion apparatus to move backward to a predetermined scale. During injection, the push rod is pressed to enable the medicine vial to output a predetermined dose of medicament liquid. The syringe of the present invention can adjust the injection dose according to the needs of different injection objects.

The syringe of the present invention further utilizes rotating the push rod of the adjustable propulsion apparatus, and the screw rod screwed in the push rod is driven to move forward spirally by the force of the rotation of the push rod until the rubber stopper connecting portion at the front end of the screw rod abuts against the rubber stopper in the medicine vial. Then the zeroing nut base is pressed forward into the rotating knob to be in a locked state. After that, rotate the zeroing nut in a clockwise direction until contacting and engaging the bottom gear disk at the rear end of the push rod, and then rotating the nut fixing piece to turn to make the zeroing nut fixed on the zeroing nut base, and the zeroing step is completed. Therefore, the syringe has the function of initial resetting when the injection dose is adjusted to ensure that the injection dose is adjusted more accurately.

DETAILED DESCRIPTION OF PREFERRED EMBODIMENT

The following describes the technical means adopted by the present invention to achieve the intended purpose of the invention in conjunction with the drawings and the preferred embodiments of the present invention.

Figure 1:
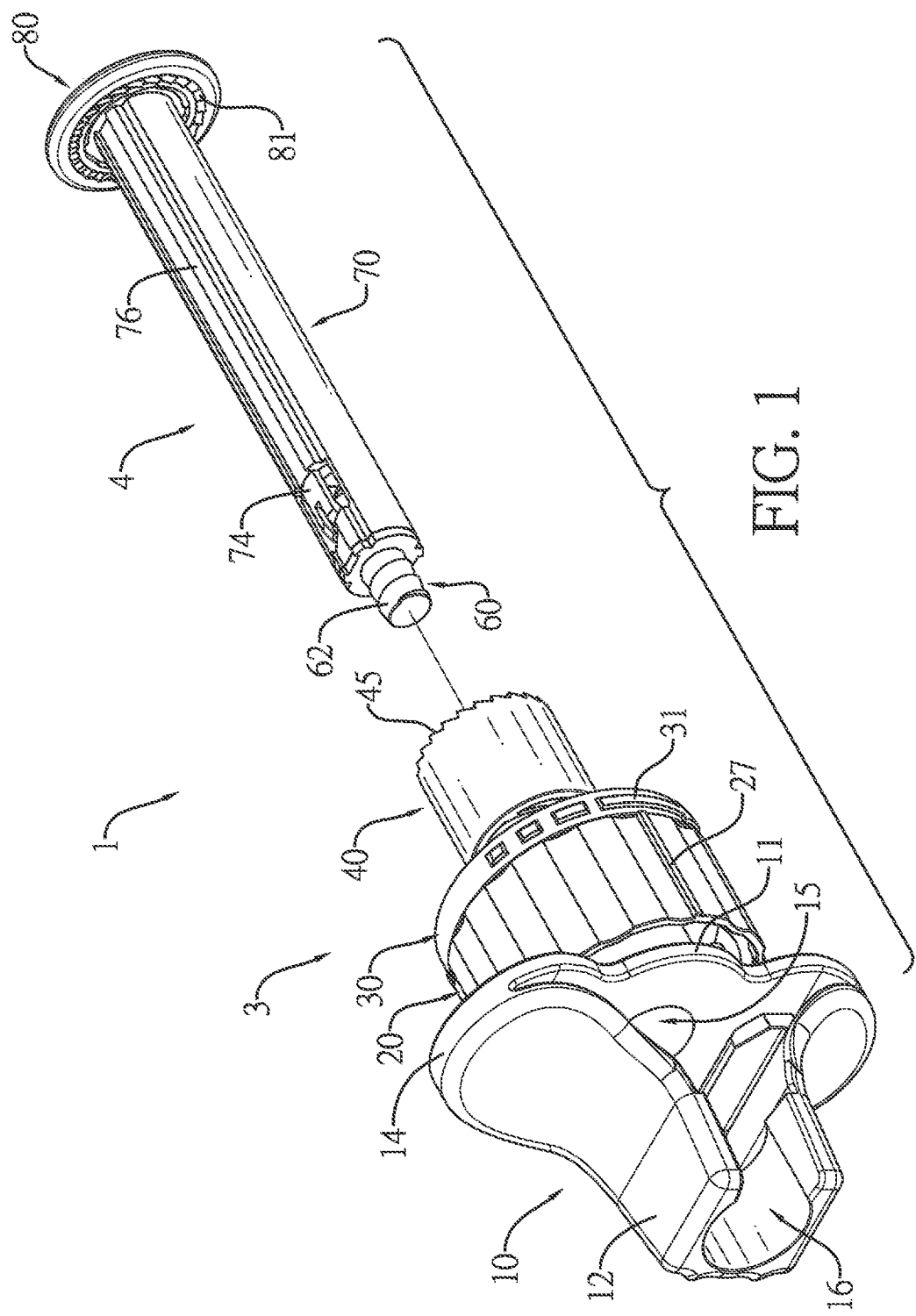
FIG. 1 is an exploded perspective view of a medicine vial connecting apparatus and an adjustable propulsion apparatus in a preferred embodiment of a syringe in accordance with the present invention.
Figure 2:
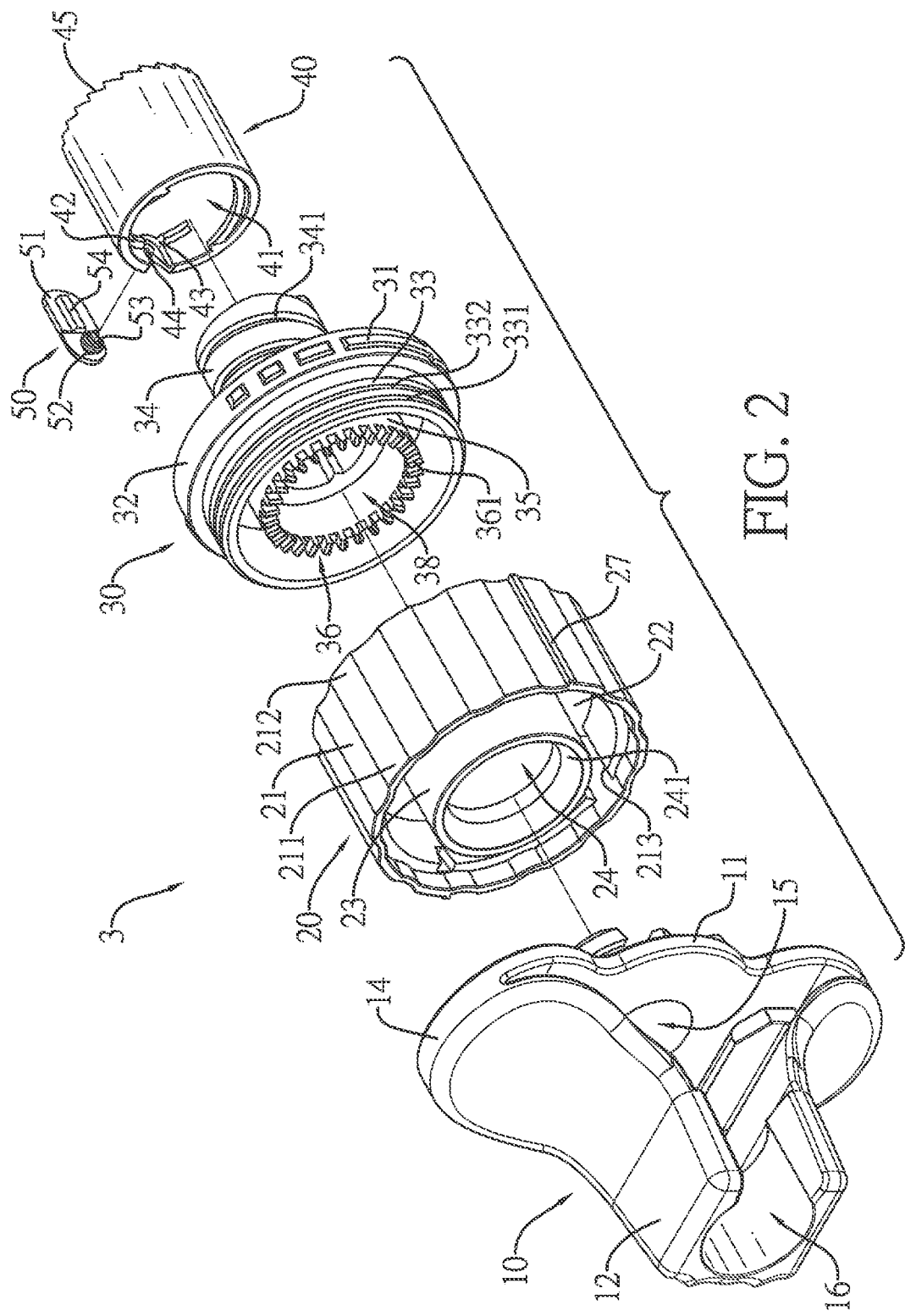
FIG. 2 is an exploded perspective view of the medicine vial connecting apparatus in FIG. 1.
Figure 3:
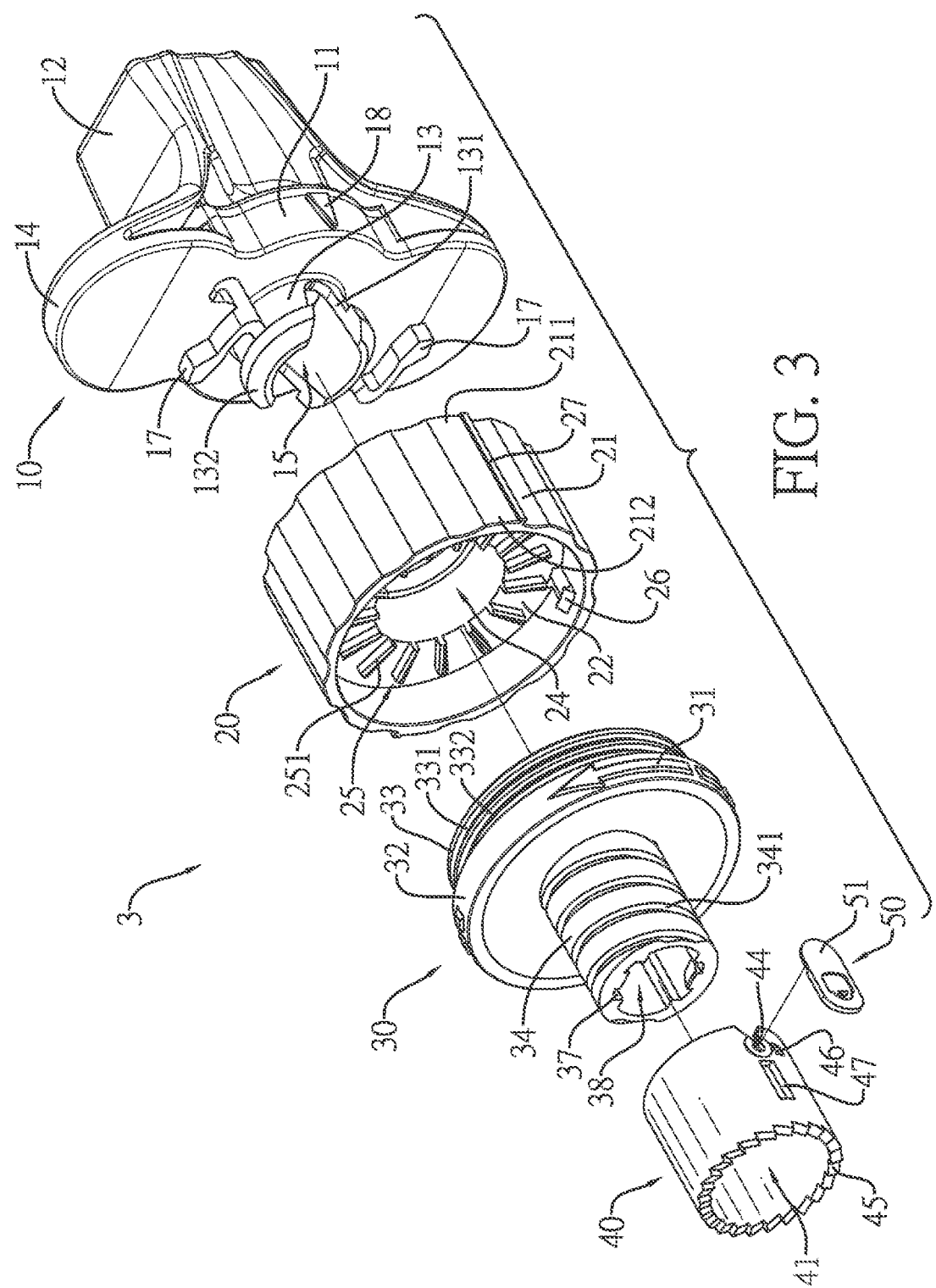
FIG. 3 is another exploded perspective view of the medicine vial connecting apparatus in FIG. 1.
Figure 4:
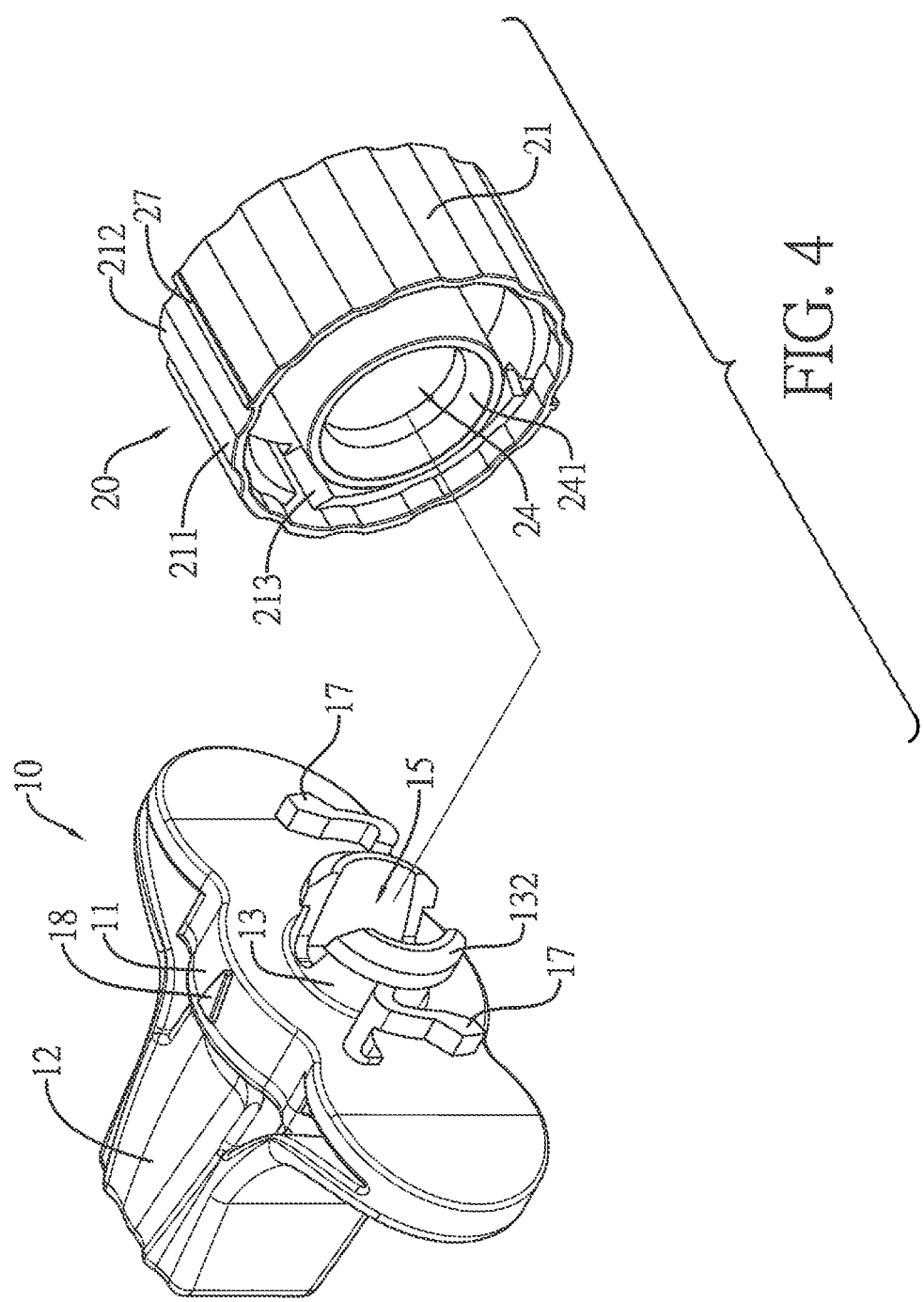
FIG. 4 is an exploded perspective view of a housing and a rotating knob of the medicine vial connecting apparatus in FIGS. 2 and 3.
Figure 12:
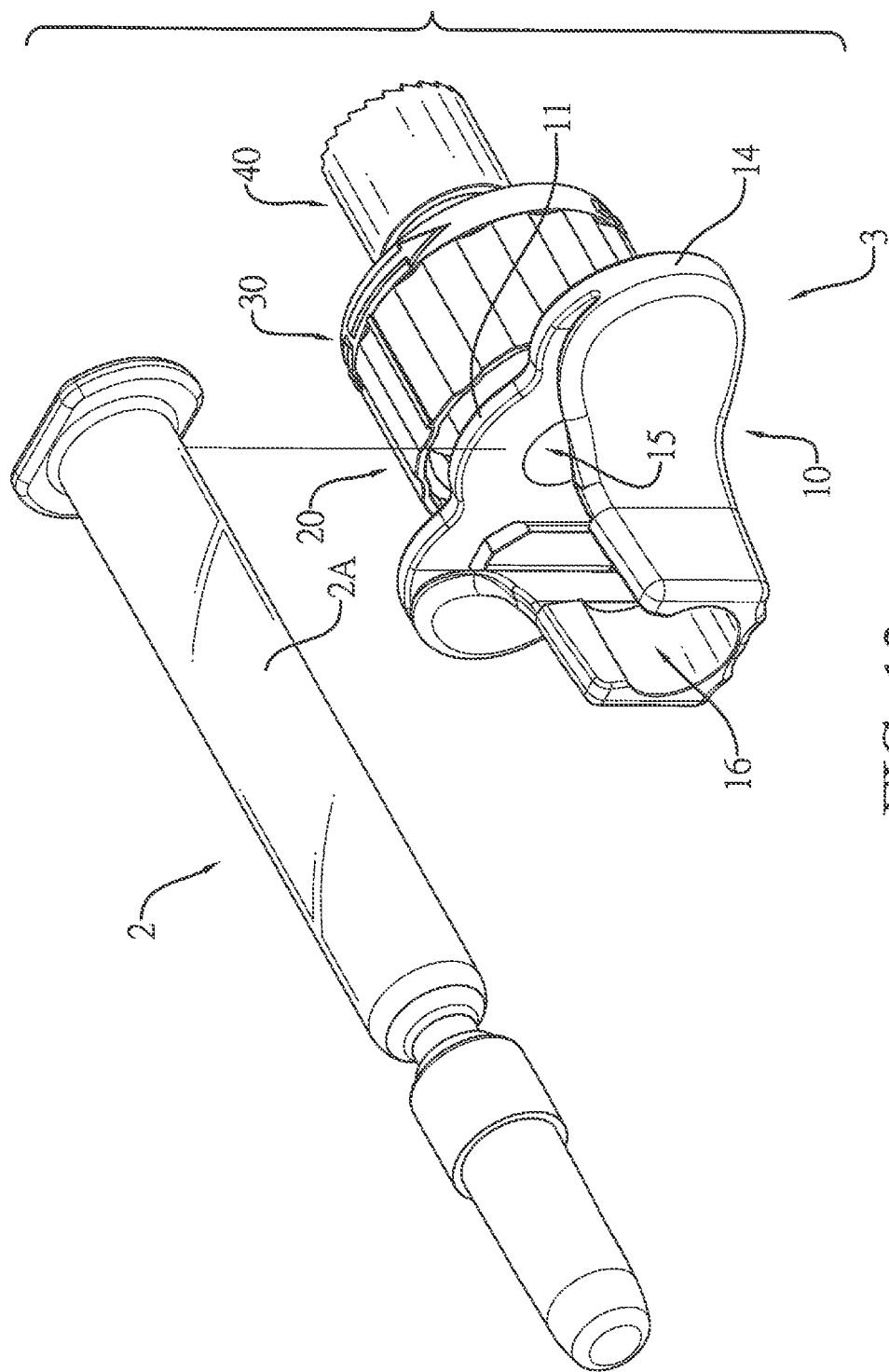
FIG. 12 is an exploded perspective view of a medicine vial before being assembled to the medicine vial connecting apparatus.
Figure 13:
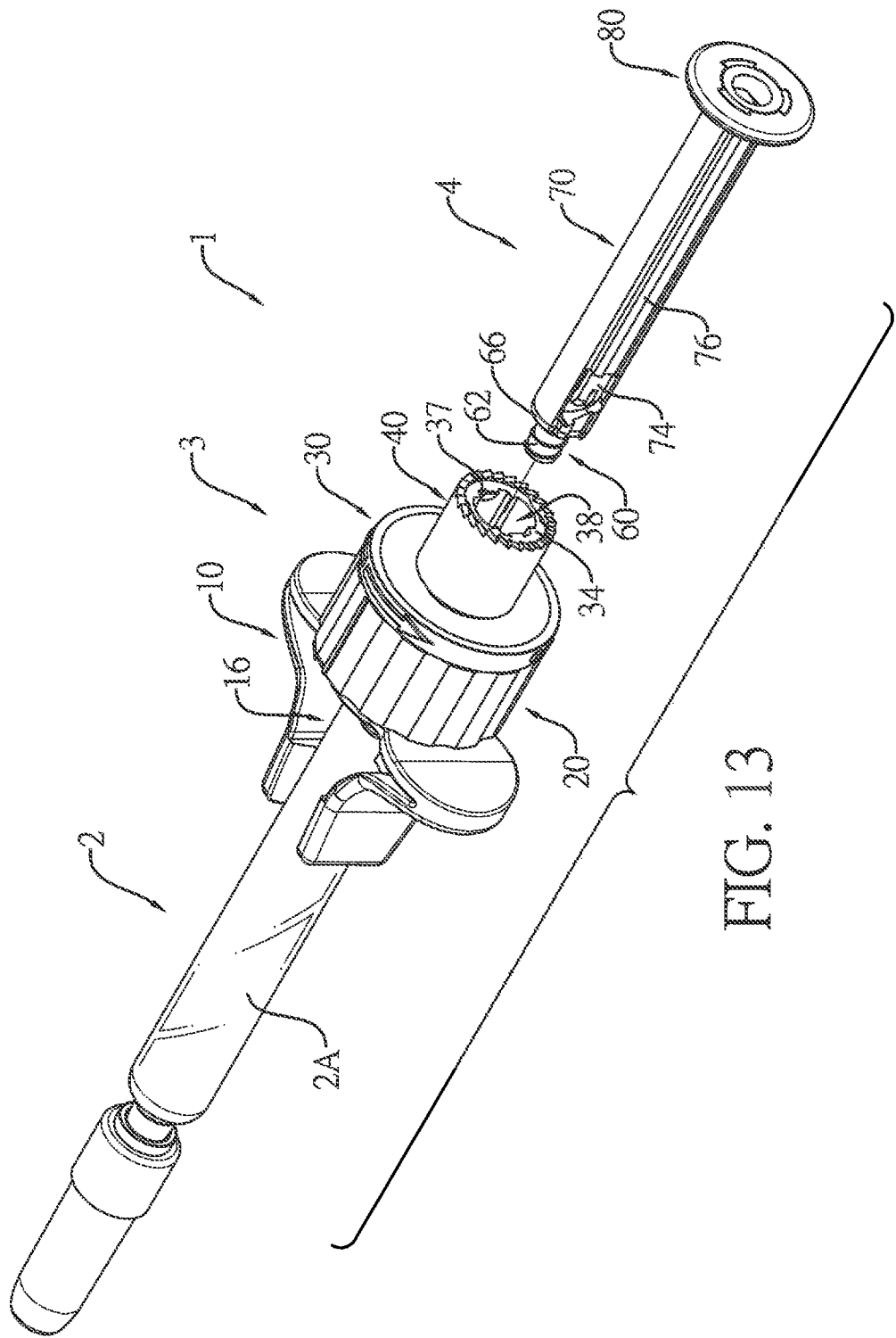
FIG. 13 is an exploded perspective view of the adjustable propulsion apparatus ready to be assembled after the medicine vial connecting apparatus is assembled to connect the medicine vial.
Figure 19:
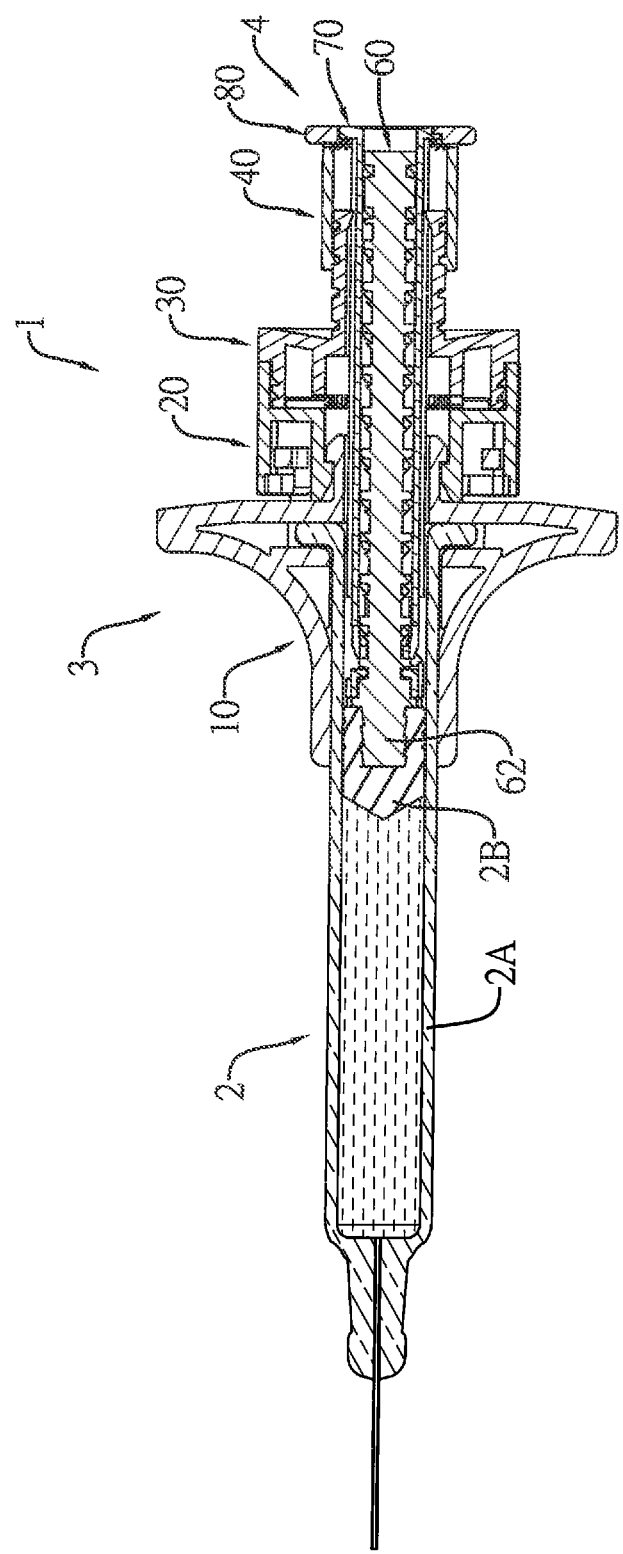
FIG. 19 is an operational cross-sectional side view of the syringe of the present invention combined with the medicine vial after the zeroing adjustment.
Figure 20:
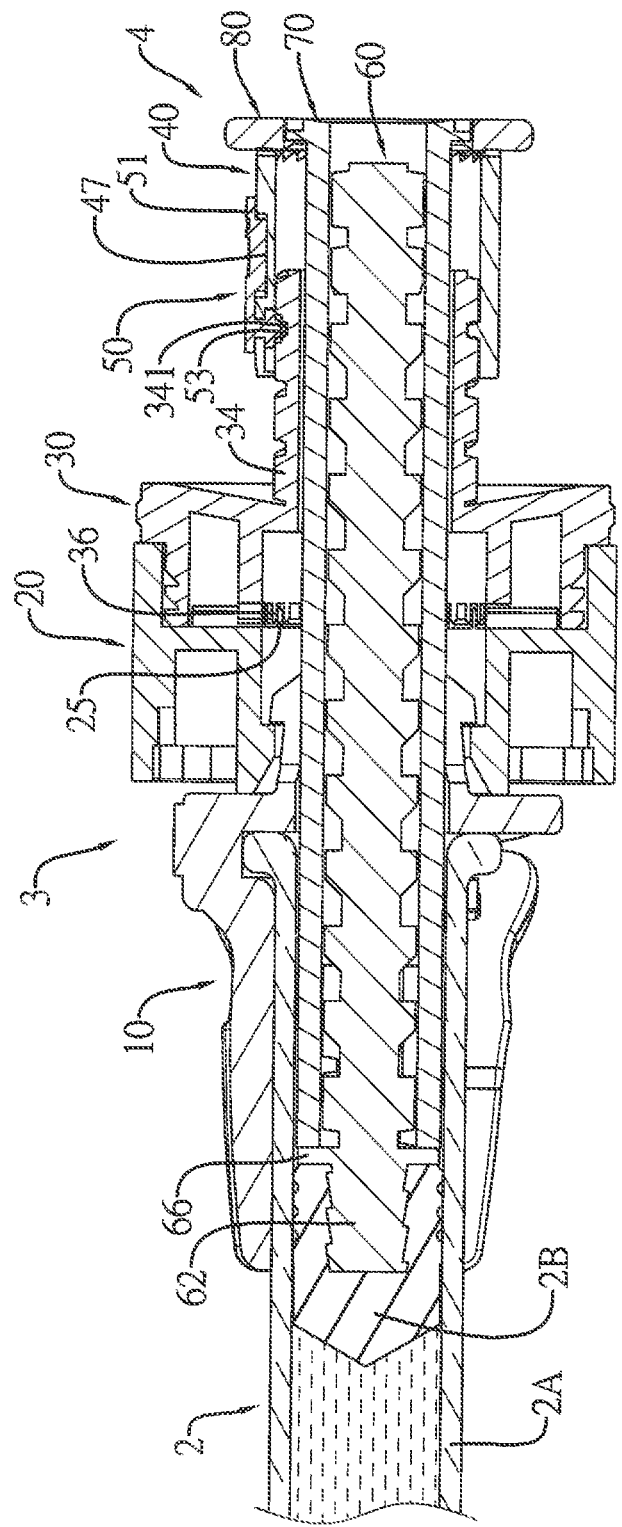
FIG. 20 is a partial enlarged cross-sectional side view of FIG. 19.

With reference to FIG. 1, a preferred embodiment of a syringe with an injection dose adjustment function of the present invention is disclosed. With reference to FIGS. 12 and 19, the syringe 1 is used for assembling a medicine vial 2, and the medicine vial 2 contains a medicine liquid and a rubber stopper 2B in a bottle 2A thereof. The bottle 2A has a needle disposed on a front end thereof and a needle sheath covering the needle. The syringe 1 includes a medicine vial connecting apparatus 3 and an adjustable propulsion apparatus 4.

With reference to FIGS. 2 to 6, the medicine vial connecting apparatus 3 is used to assemble the medicine vial 2. The medicine vial connecting apparatus 3 includes a housing 10, a rotating knob 20, and a zeroing nut base 30, or further includes a zeroing nut 40 and a nut fixing piece 50.

With reference to FIGS. 2 to 6, the housing 10 includes a housing base 11, a medicine vial assembly portion 12, and a joining pipe portion 13. The medicine vial assembly portion 12 and the joining pipe portion 13 are respectively formed on a front end and a rear end of the housing base 11. The housing base 11 has two side wing portions 14 formed on and protruding outwardly from two sides thereof, respectively. The two side wing portions 14 extend to the medicine vial assembly portion 12. The housing 10 has a housing middle hole 15 extending from the front end of the housing base 11 to a rear end of the joining pipe portion 13. The medicine vial assembly portion 12 has an assembly groove 16 formed therein and communicating with the housing middle hole 15. The medicine vial assembly portion 12 has a front opening and a side opening respectively formed at a front end and a side of the assembly groove 16 and communicating with each other. Then the medicine vial 2 can be assembled in the assembly groove 16 laterally through the side opening and the front opening of the medicine vial assembly portion 12, the bottle 2A of the medicine vial 2 can be fixed in the medicine vial assembly portion 12, and a rear opening of the bottle 2A of the medicine vial 2 corresponds to the housing middle hole 15.

With reference to FIGS. 2 to 6, in the housing 10, two unidirectional snap hooks 17 are formed on an outer side of the joining pipe portion 13 at a rear side of the housing base 11 to provide positioning and generate a sound. In the preferred embodiment shown in FIGS. 2 to 6, the joining pipe portion 13 of the housing 10 has two recesses 131, the recesses 131 extend forward from the rear end of the joining pipe portion 13 so that the joining pipe portion 13 has retracting and restoring elasticity, and a limiting flange 132 is formed on an outer peripheral surface at the rear end of the joining pipe portion 13.

With reference to FIGS. 2 to 6, the housing 10 can also be provided with an indicator mark 18 on an outer peripheral surface of the housing base 11, the indicator mark 18 corresponds to a center line of the housing 10, and the indicator mark 18 provides auxiliary marks for adjustment of alignment.

With reference to FIGS. 2 to 6, the rotating knob 20 is rotatably arranged on the outer side of the joining pipe portion 13 of the housing 10. The rotating knob 20 is located at the rear side of the housing base 11, since the joining pipe portion 13 of the housing 10 has the flexibility of retracting and restoring, the rotating knob 20 can be easily assembled to the joining pipe portion 13, and the limiting flange 132 at the rear end of the joining pipe portion 13 limits the position of the rotating knob 20 to prevent the rotating knob 20 detaching from the joining pipe portion 13.

With reference to FIGS. 2 to 6, the rotating knob 20 includes a knob shell 21, a knob inner plate 22, a knob inner tube 23, and an inner hole 24. The knob shell 21 is a hollow shell and has a shell front section 211 and a shell rear section 212. The knob inner plate 22 is formed in the knob shell 21 between the shell front section 211 and the shell rear section 212. The knob inner tube 23 is disposed in the shell front section 211, and the shell front section 211 has two unidirectional buckle grooves 213 formed on an inner peripheral wall thereof.

With reference to FIGS. 2 to 6, the knob inner tube 23 is connected to a front end of the knob inner plate 22, and the inner hole 24 is provided in the knob inner tube 23 and the knob inner plate 22, that is, the inner hole 24 extends from a front end of the knob inner tube 23 rearward and is formed through the knob inner plate 22. The rotating knob 20 has an annular stop 241 formed on the inner peripheral wall of the inner hole 24. With the annular stop 241, the joining pipe portion 13 of the housing 10 is pivotally connected in the inner hole 24 of the rotating knob 20. The position of the rotating knob 20 is limited by a cooperation between the limiting flange 132 at the rear end of the joining pipe portion 13 and the annular stop 241 to prevent the rotating knob 20 detaching from the joining pipe portion 13. The knob inner plate 22 has a first locking portion 25 formed on a rear side thereof, the first locking portion 25 has multiple locking flanges 251, and the multiple locking flanges 251 are arranged in a ring shape relative to a center of the inner hole 24. The knob shell 21 has an engaging portion 26 formed on an inner peripheral wall of the shell rear section 212. The rotating knob 20 can also be provided with a marking line 27 on an outer peripheral surface of the knob shell 21, and an alignment of the marking line 27 and the indicator mark 18 of the housing 10 shows whether it is correctly aligned.

With reference to FIGS. 2 to 6, the zeroing nut base 30 is connected to the shell rear section 212 of the rotating knob 20, and the zeroing nut base 30 can be rotated relative to and engage with the rotating knob 20. The zeroing nut base 30 includes a base mount 32, an assembly end portion 33, an assembly tube portion 34, and a nut inner tube 35. The assembly end portion 33 and the assembly tube portion 34 are respectively formed on a front end and a rear end of the base mount 32. The assembly end portion 33 has a pivot annular groove 331 and an engaging annular groove 332 formed on an outer peripheral surface of the assembly end portion 33 at a spaced interval. The assembly tube portion 34 has a screw thread 341 formed on an outer peripheral surface thereof. The nut inner tube 35 is disposed in the assembly end portion 33 and extends forward from the base mount 32. The zeroing nut base 30 has an inner shaft hole 38, and the inner shaft hole 38 extends from a front end of the nut inner tube 35 to a rear end of the assembly tube portion 34. The zeroing nut base 30 has at least one guide groove portion 37 formed on an inner wall of the inner shaft hole 38 and extending forward and backward axially. The nut inner tube 35 has a second locking portion 36 formed on a front end thereof, and the second locking portion 36 has multiple locking recesses 361. The assembly end portion 33 of the zeroing nut base 30 can be assembled in the shell rear section 212 of the rotating knob 20, and the engaging portion 26 of the rotating knob 20 can be selectively engaged with the pivot annular groove 331 or the engaging annular groove 332. When the engaging portion 26 is engaged with the pivot annular groove 331 at the front position, the zeroing nut base 30 can be rotated relative to the rotating knob 20. When the engaging portion 26 is engaged with the engaging annular groove 332 at the rear position, the second locking portion 36 at the front end of the nut inner tube 35 of the zeroing nut base 30 is engaged with the first locking portion 25 at the rear end surface of the knob inner plate 22 of the rotating knob 20 by concave-convex cooperation in a locked state. The zeroing nut base 30 has a rotation indicator 31 formed on an outer peripheral surface thereof to indicate a direction of rotation.

With reference to FIGS. 2 to 6, the zeroing nut 40 has a screw hole 41 formed therein. The zeroing nut 40 has a threaded strip 42 formed on an inner wall of the screw hole 41. The threaded strip 42 has a vacant portion 43 formed thereon. The zeroing nut 40 has a pivot hole 44 formed on a peripheral wall thereof, and a position of the pivot hole 44 corresponds to that of the vacant portion 43. The zeroing nut 40 has a first engaging segment 45 formed on a rear end thereof, and the first engaging segment 45 has multiple single oblique first teeth. The zeroing nut 40 is screwed on the outer side of the assembly tube portion 34 of the zeroing nut base 30, and the threaded strip 42 is screwed to the screw thread 341.

With reference to FIGS. 2 to 9, the nut fixing piece 50 includes a sheet 51, a pivot 52, and a protruding portion 53. The pivot 52 is disposed on an end side of the sheet 51, and the protruding portion 53 is disposed on the pivot 52 opposite to the sheet 51. The nut fixing piece 50 is pivotally mounted in the pivot hole 44 of the zeroing nut 40 by the pivot 52. The sheet 51 is located on an outer side of the zeroing nut 40, and the protruding portion 53 is located in the vacant portion 43 of the threaded strip 42 of the zeroing nut 40. The nut fixing piece 50 can rotate relative to the zeroing nut 40, so that the protruding portion 53 and the threaded strip 42 form a continuous spiral bar, and can be screwed with the screw thread 341 of the zeroing nut base 30. Alternatively, the protruding portion 53 can be deflected at the position of the vacant portion 43 of the threaded strip 42 and can interfere with the screw thread 341 of the zeroing nut base 30.

With reference to FIGS. 2 to 6, the zeroing nut 40 has a first positioning recess 46 and a second positioning recess 47 formed on the peripheral wall thereof at two different sides relative to the pivot hole 44, and the sheet 51 of the nut fixing piece 50 has a positioning flange 54 formed on a side surface of the sheet 51 facing the zeroing nut 40. The positioning flange 54 can be selectively engaged with the first positioning recess 46 and the second positioning recess 47 with the rotation of the nut fixing piece 50.

Figure 10:
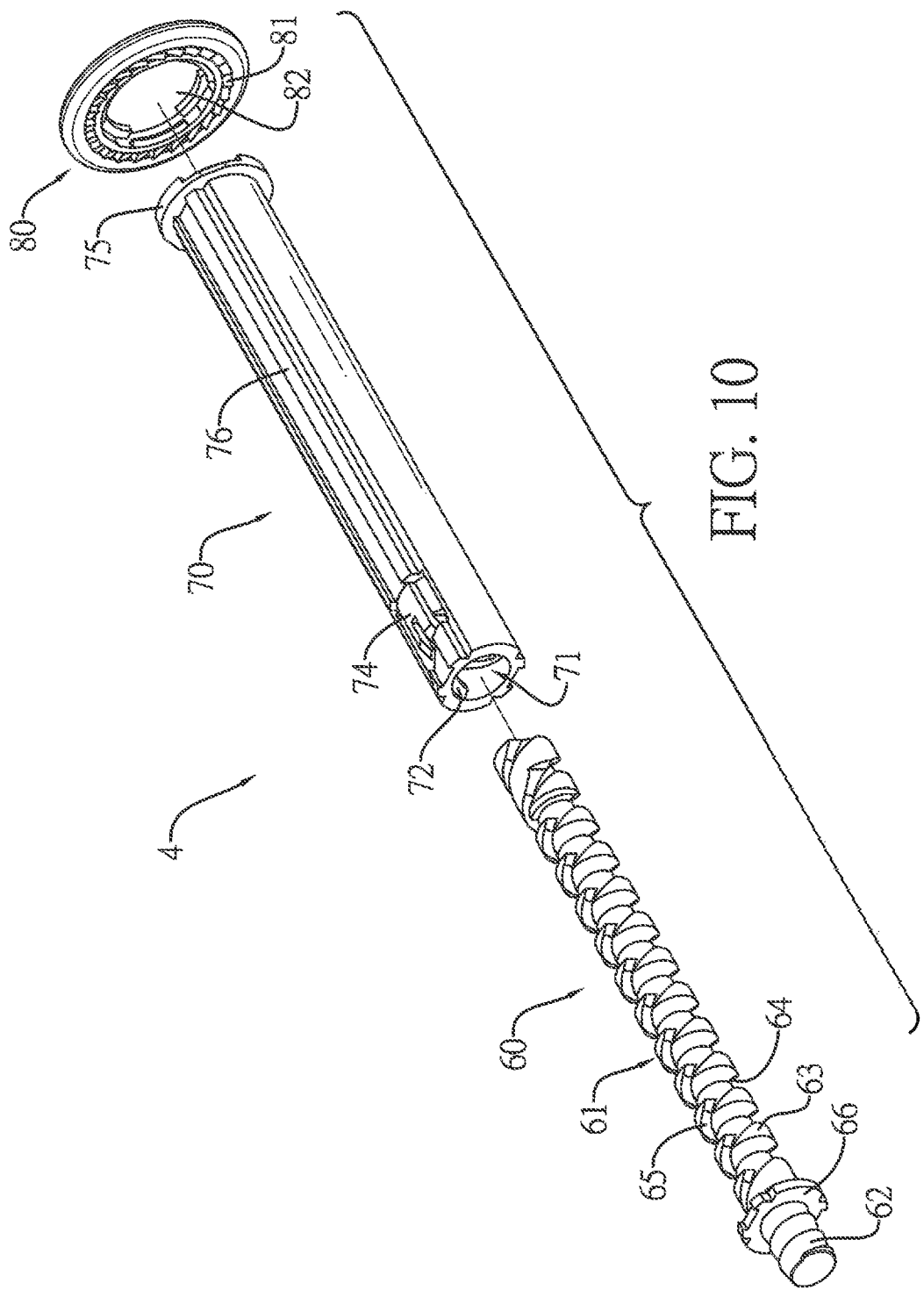
FIG. 10 is an exploded perspective view of the adjustable propulsion apparatus in FIG. 1.
Figure 11:
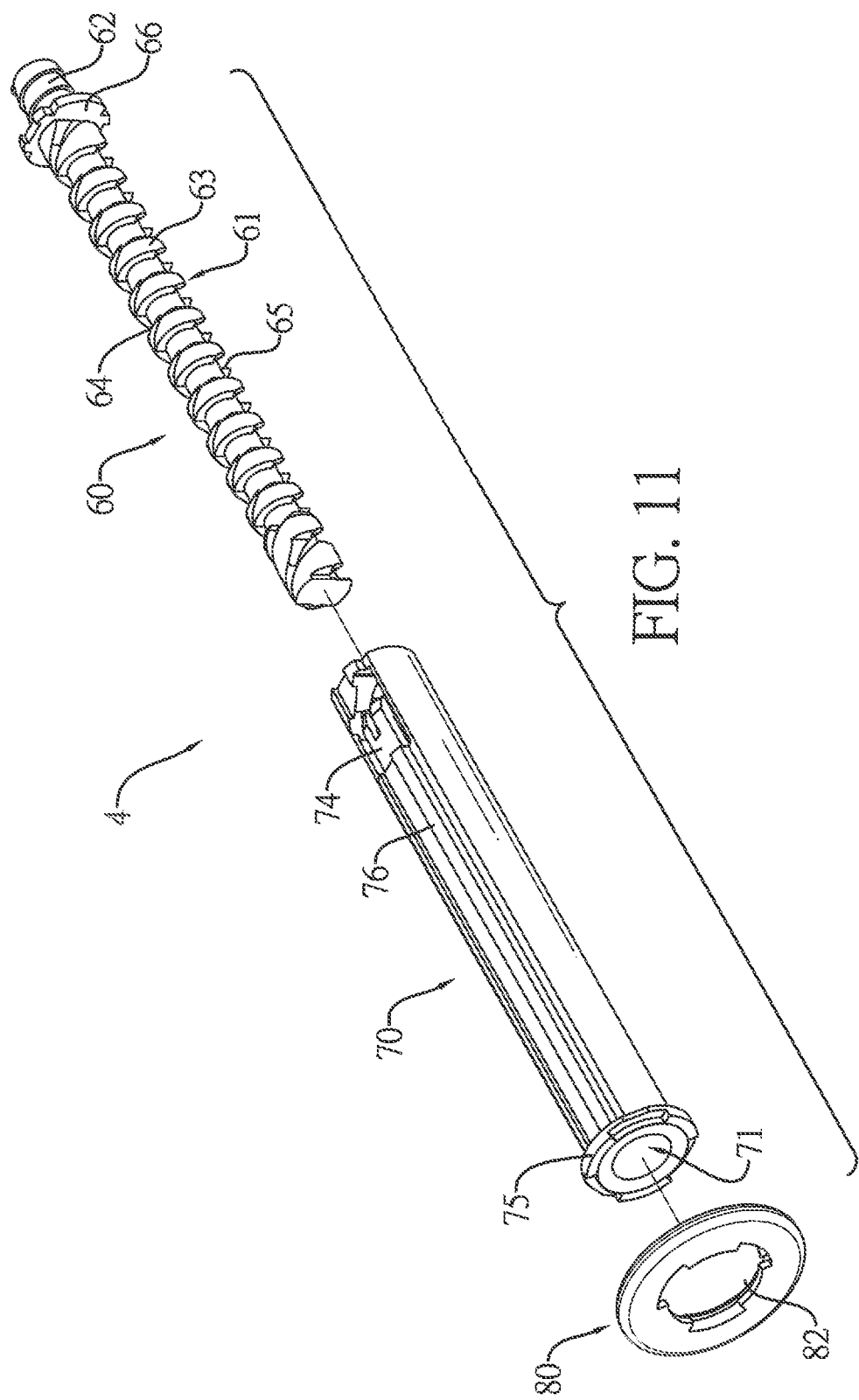
FIG. 11 is another exploded perspective view of the adjustable propulsion apparatus in FIG. 1.

With reference to FIGS. 10 to 12, the adjustable propulsion apparatus 4 is mounted through the medicine vial connecting apparatus 3 and extends into the medicine vial 2 to push against the rubber stopper 2B, and the adjustable propulsion apparatus 4 includes a screw rod 60 and a push rod 70, and further includes a bottom gear disk 80.

With reference to FIGS. 10 to 12, the screw rod 60 includes a screw body 61 and a rubber stopper connecting portion 62. The screw body 61 has multiple screwing units 63 formed on an outer peripheral surface of the screw body 61, and the multiple screwing units 63 are equally spaced along an axial direction of the screw body 61, sequentially. An annular slot 64 is formed between each two adjacent said screwing units 63, and each screwing unit 63 has one or more spiral grooves 65. A front end and a rear end of the spiral groove 65 of each screwing unit 63 are respectively connected to the annular slots 64 at a front position and a rear position of the screwing unit 63. The rubber stopper connecting portion 62 is formed at a front end of the screw body 61. The rubber stopper connecting portion 62 is used to connect the rubber stopper 2B in the medicine vial 2. A stop portion 66 is formed on the screw rod 60 between the rubber stopper connecting portion 62 and the screw body 61.

With reference to FIGS. 10 to 12, the push rod 70 has a push rod hole 71 formed therein and a threaded portion 72 formed on an inner wall of the push rod hole 71. The screw rod 60 is assembled in the push rod hole 71 of the push rod 70, and the threaded portion 72 of the push rod 70 is threaded with the spiral grooves 65 of the screw rod 60. Then the screw rod 60 can rotate and move back and forth in the push rod 70, and the stop portion 66 of the screw rod 60 can limit the positon of the screw rod 60 at a front end of the push rod 70. The threaded portion 72 is formed on a front section of the inner wall of the push rod hole 71, and the push rod 70 further has at least one push arm 74. In the preferred embodiment, the push rod 70 has two push arms 74, and the two push arms 74 are arranged oppositely in a radial direction. A front end of the push arm 74 is a free end, so that the push arm 74 can be bent and deformed and extend into the push rod hole 71. In addition, the push arm 74 can extend into the annular slot 64 of the screw rod 60 and press against an end surface of the screwing unit 63.

Figure 22:
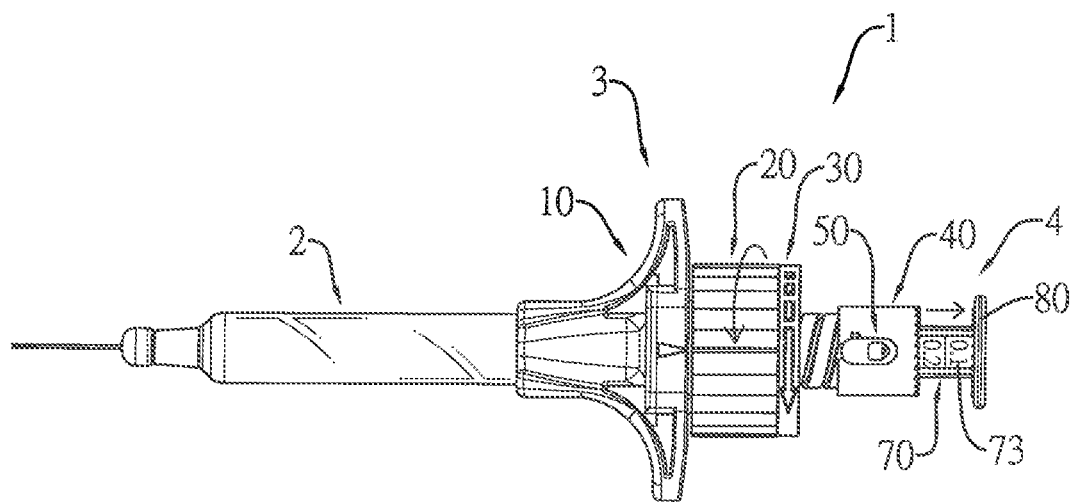

With reference to FIG. 22, the push rod 70 has a scale 73 formed on an outer peripheral surface thereof. The push rod 70 is assembled in the zeroing nut base 30. The push rod 70 can move linearly relative to the zeroing nut base 30, and the push rod 70 can rotate with the zeroing nut base 30 together. In the preferred embodiment, the push rod 70 has a guide rail portion 76 formed on the outer peripheral surface thereof and extending axially. The guide rail portion 76 corresponds to the guide groove portion 37 in the zeroing nut base 30, so that the push rod 70 can be moved relative to the zeroing nut base 30 linearly, and the push rod 70 can be rotated together with the zeroing nut base 30.

With reference to FIGS. 10 to 12, the push rod 70 further has a gear disk fixed portion 75 disposed on a rear end of the push rod 70, and the bottom gear disk 80 has a fixing hole 82. The gear disk fixed portion 75 of the push rod 70 is securely connected to the fixing hole 82 of the bottom gear disk 80. The bottom gear disk 80 has a second engaging segment 81 formed on a front side thereof, and the second engaging segment 81 has multiple single oblique second teeth. The second engaging segment 81 can selectively engage with the first engaging segment 45 at the rear end of the zeroing nut 40.

When the syringe 1 is in use, in an initial state, as shown in FIG. 1, the medicine vial connecting apparatus 3 and the adjustable propulsion apparatus 4 are in a separated state, and the operation steps are as follows.

With reference to FIG. 12, in a step of connecting the syringe to the medicine vial 2, first, assemble the medicine vial 2 in the medicine vial connecting apparatus 3, wherein the medicine vial 2 is installed in the medicine vial assembly portion 12 of the housing 10 by side insertion, and a mouth at a rear end of the bottle 2A of the medicine vial 2 corresponds to the housing middle hole 15 of the housing base 11, and then the adjustable propulsion apparatus 4 is passed through the medicine vial connecting apparatus 3 and extends into the medicine vial 2. At this time, the zeroing nut 40 can rotate relative to the rotating knob 20, and the zeroing nut 40 is located in front of the bottom gear disk 80 of the adjustable propulsion apparatus 4. The zeroing nut 40 and the bottom gear disk 80 are not engaged with each other.

Figure 8:
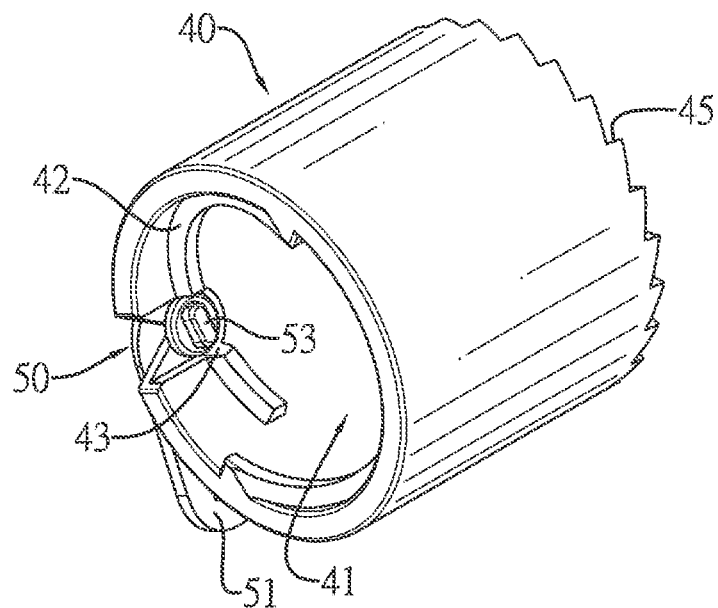
FIG. 8 is a perspective view of a zeroing nut and a nut fixing piece of the medicine vial connecting apparatus in FIGS. 1 to 3 before being locked.
Figure 9:
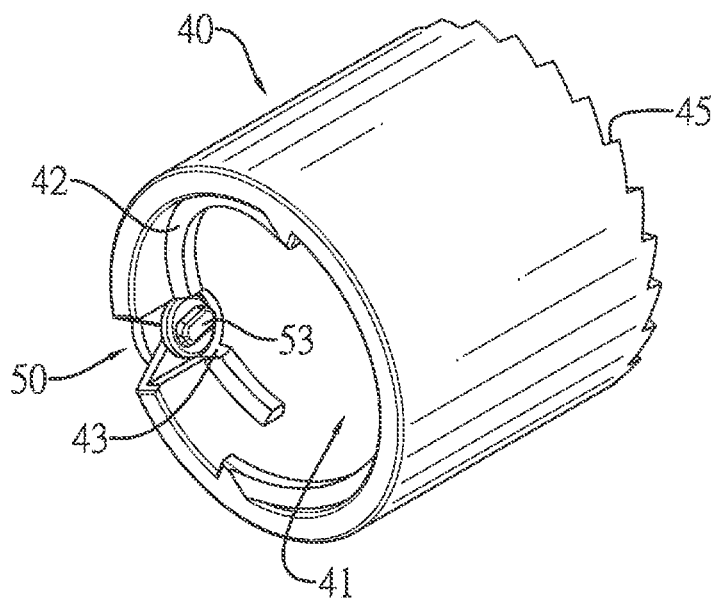
FIG. 9 is a perspective view of the zeroing nut and the nut fixing piece of the medicine vial connecting apparatus in FIGS. 1 to 3 after being locked.
Figure 14:
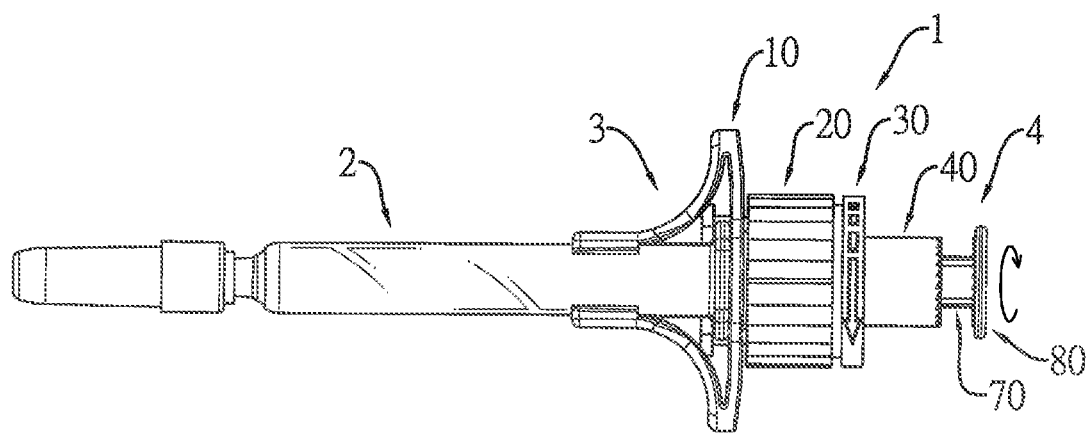
FIGS. 14 to 16 are operational side views of a zeroing adjustment of the syringe of the present invention.
Figure 15:
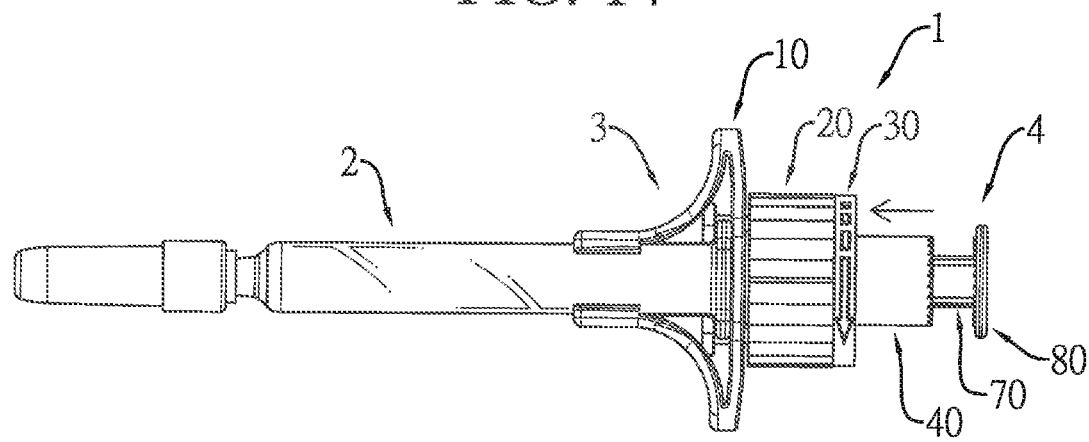
Figure 16:
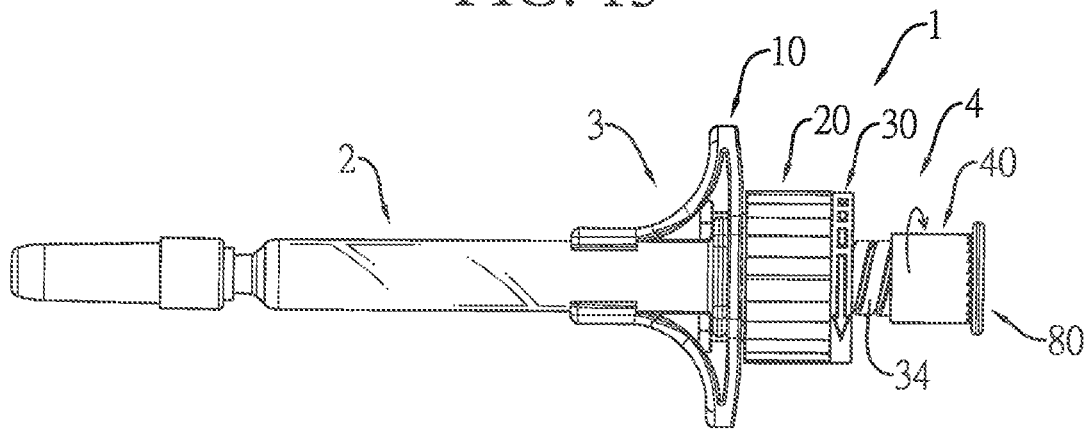
Figure 17:
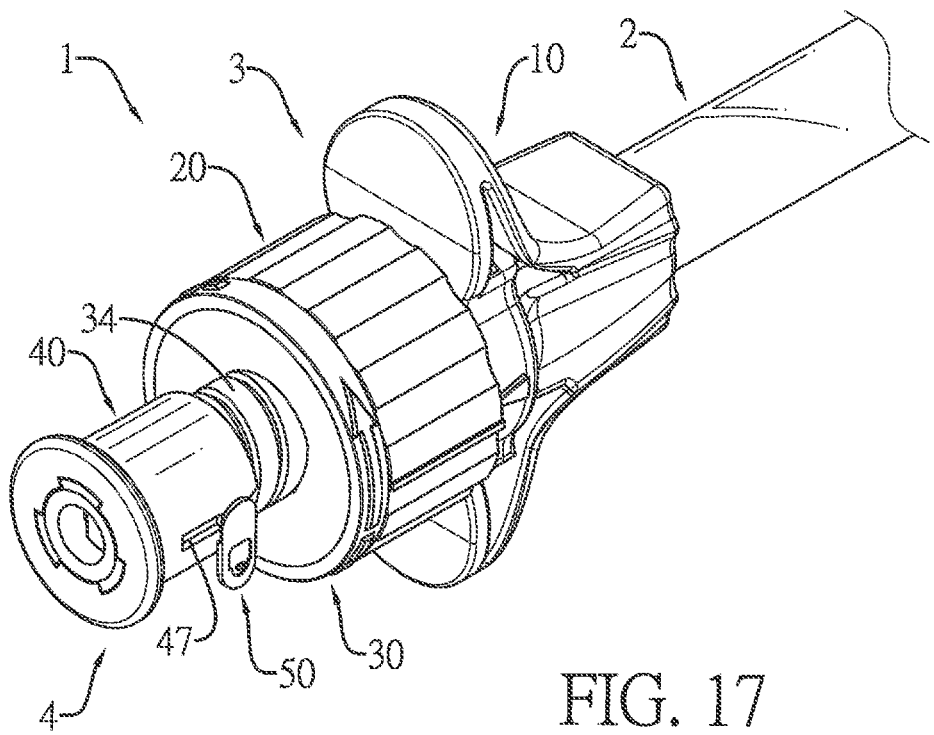
FIGS. 17 and 18 are operational perspective views of the operation of locking the return-to-zero nut on the return-to-zero nut base by using the nut fixing plate after the return-to-zero adjustment of the syringe of the present invention.
Figure 18:
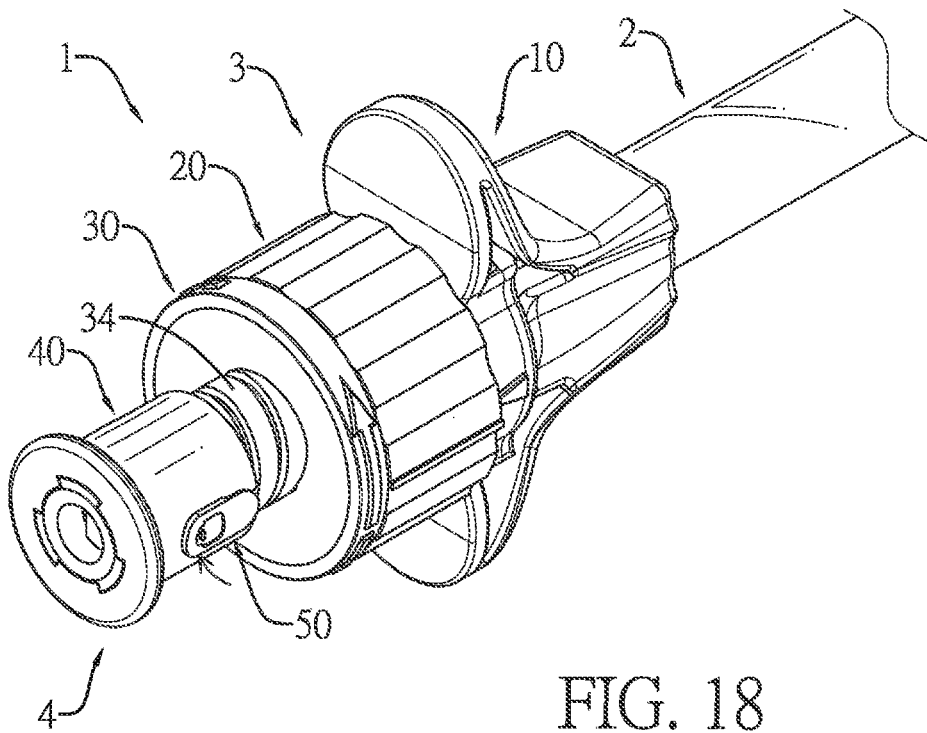

With reference to FIGS. 14 to 16, in a step of resetting the syringe 1 to zero, wherein the push rod 70 of the adjustable propulsion apparatus 4 is rotated, and the force of the rotation of the push rod 70 drives the screw rod 60 screwed in the push rod 70 to move forward to enable the rubber stopper connecting portion 62 at the front end of the screw rod 60 to abut against the rubber stopper 2B in the medicine vial. Then press the zeroing nut base 30 forward into the rotating knob 20, so that the engaging portion 26 of the rotating knob 20 is engaged with the engaging annular groove 332 at the rear of the zeroing nut base 30. The second locking portion 36 at the front end of the nut inner tube 35 of the zeroing nut base 30 and the first locking portion 25 on the rear end surface of the knob inner plate 22 of the rotating knob 20 are in concave-convex cooperation to be in a locked state. After that, rotate the zeroing nut 40 in a clockwise direction to contact the bottom gear disk 80 at the rear end of the push rod 70, and the first engaging segment 45 at the rear end of the zeroing nut 40 engages with the second engaging segment 81 on the front end surface of the bottom gear disk 80. With reference to FIGS. 8 and 9, rotate the nut fixing piece 50 to turn, so that the zeroing nut 40 is fixed on the zeroing nut base 30, the zeroing nut 40 is fixed and cannot be moved, and the zeroing step is completed.

In the step of resetting the syringe 1 after the medicine vial 2 is assembled, as shown in FIGS. 17 to 18 and FIGS. 8 to 9, turn the rotating nut fixing piece 50, and the protruding portion 53 of the nut fixing piece 50 is deflected at the position of the vacant portion 43 of the threaded strip 42 of the zeroing nut 40 and interferes with the screw thread 341 of the zeroing nut base 30. Then the zeroing nut 40 is fixed on the zeroing nut base 30, and the zeroing nut 40 is fixed and cannot move. On the other hand, the positioning flange 54 of the sheet 51 of the nut fixing piece 50 facing the side surface of the zeroing nut 40 is engaged in the second positioning recess 47 to achieve a stable locking state.

Figure 21:
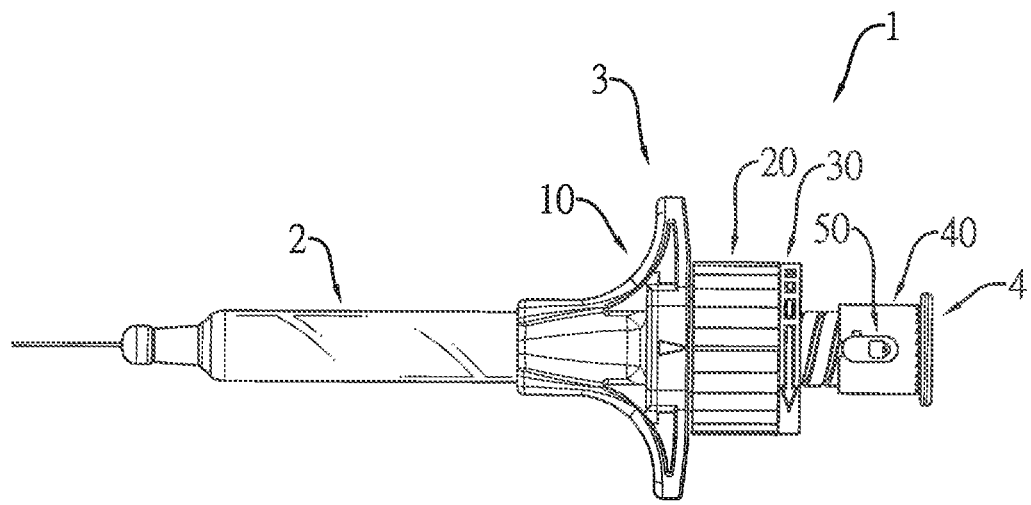
FIGS. 21 and 22 are operational side views of the syringe of the present invention for adjusting an injection dose.
Figure 23:
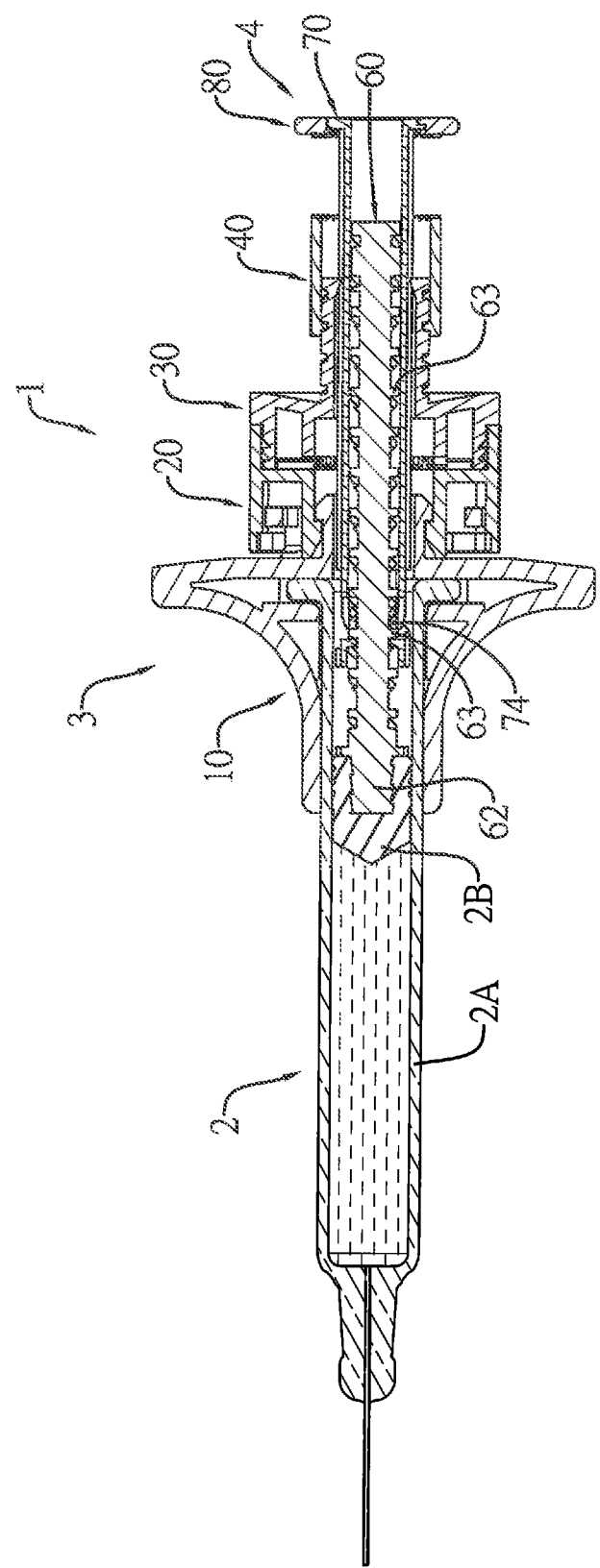
FIG. 23 is an operational cross-sectional side view of the syringe of the present invention completing an adjustment of injection dose.

With reference to FIGS. 21 to 23, in a step of adjusting the injection dose of the syringe 1, rotate the rotating knob 20 (in a counterclockwise direction). Each time the knob 20 is rotated, a fixed angle is adjusted by one unit (in the preferred embodiment, 1 unit is set as the injection dose of 0.1 ml), until it is adjusted to the scale required by the person receiving the injection.

Figure 6:
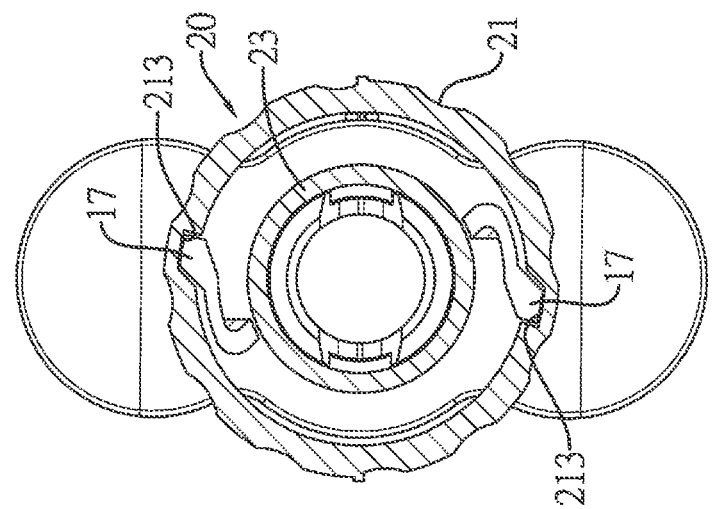
FIG. 6 is an end cross-sectional side view along a line A-A in FIG. 5.
Figure 5:
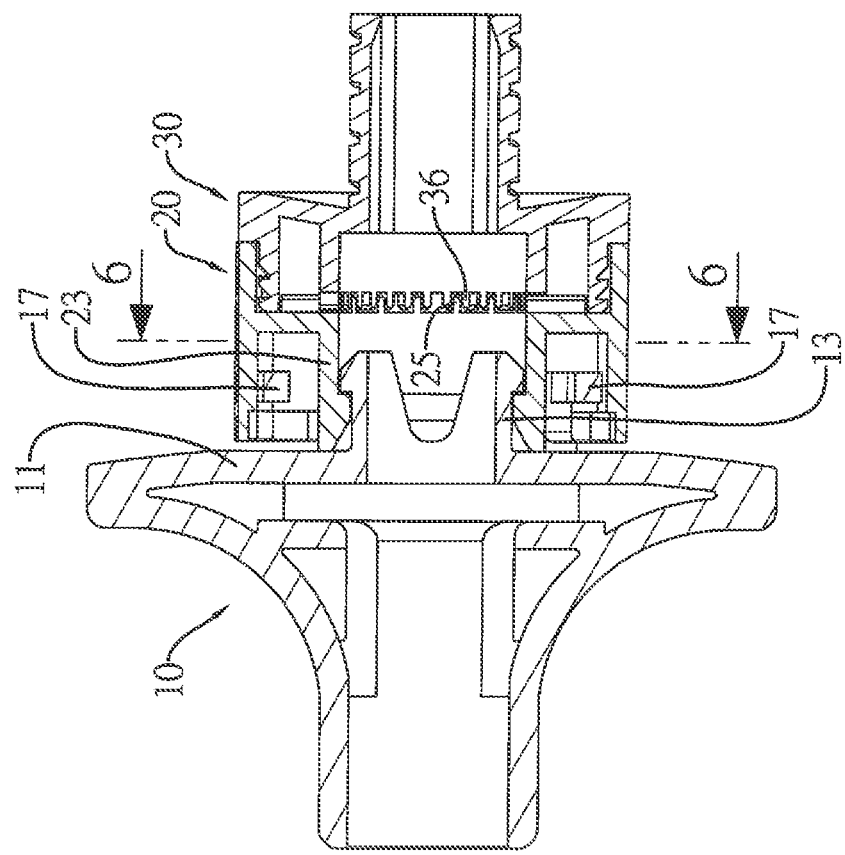
FIG. 5 is a cross-sectional side view of the housing, the rotating knob, and a zeroing nut base of the medicine vial connecting apparatus in FIGS. 1 to 3.
Figure 7:
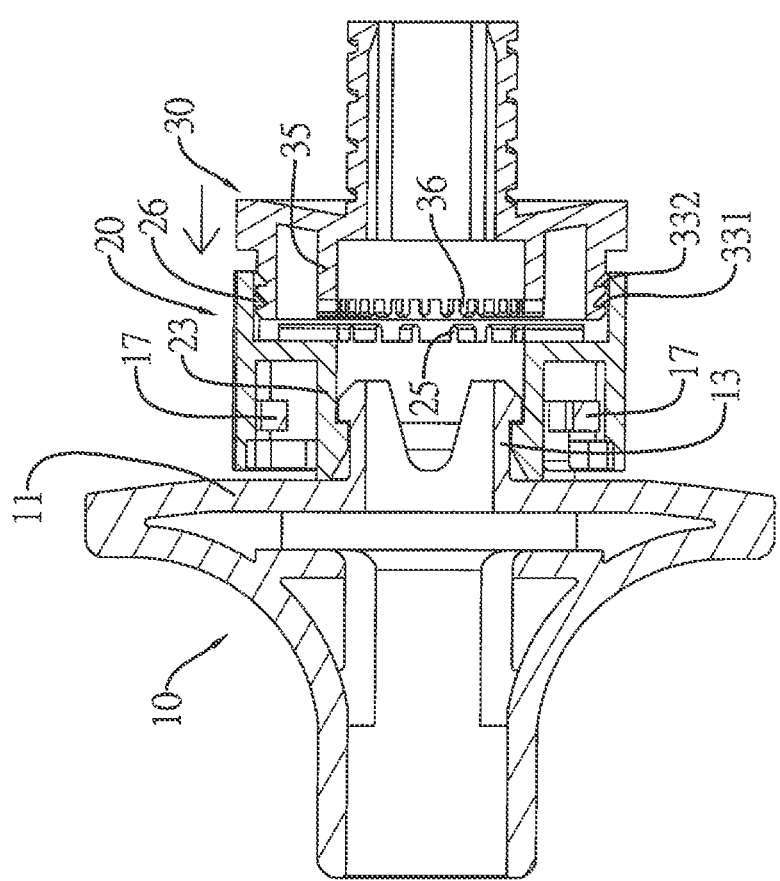
FIG. 7 is a cross-sectional side view of the rotating knob and the zeroing nut base of the medicine vial connecting apparatus in FIGS. 1 to 3 before being locked.

In the step of adjusting the injection dose of the syringe 1, as shown in FIGS. 5 and 6, the syringe 1 uses a combined structure of the two unidirectional snap hooks 17 at the rear end of the housing 10 with equal angles and the two unidirectional buckle grooves 231 on the inner peripheral wall of the shell front section 211 of the rotating knob 20 with equal angles to limit the rotation of the rotating knob 20 to a fixed scale and can no longer be reversely rotated, and makes the rotating knob 20 have an obvious positioning sound every time to use sound for recognition of injection dose adjustment for the users.

With reference to FIG. 23, in an injection step, the user can start pressing the push rod 70 to move forward after adjusting the required scale 73 of the injection dose, and push the rubber stopper 2B in the medicine vial 2 by the screw rod 60 to push the medicament liquid output in the medicine vial 2 until the bottom gear disk 80 at the rear end of the push rod 70 contacts the zeroing nut 40, and the injection is completed.

According to the above description, the syringe 1 of the present invention mainly uses the combined structure of the medicine vial connecting apparatus 3 and the adjustable propulsion apparatus 4, the medicine vial connecting apparatus 3 is assembled to the medicine vial 2, and then installed in the adjustable propulsion apparatus 4. That is, the rotating knob 20 of the medicine vial connecting apparatus 3 can be used to drive the push rod 70 of the adjustable propulsion apparatus 4 to move backward to a predetermined scale. During injection, the push rod 70 is pressed to enable the medicine vial 2 to output a predetermined dose of medicament liquid. The syringe 1 of the present invention can adjust the injection dose according to the needs of different injection objects.

Furthermore, the syringe 1 of the present invention can also be used by rotating the push rod 70 of the adjustable propulsion apparatus 4, and the screw rod 60 screwed in the push rod 70 is driven to move forward spirally by the force of the rotation of the push rod 70 until the rubber stopper connecting portion 62 at the front end of the screw rod 60 abuts against the rubber stopper 2B in the medicine vial 2. Then the zeroing nut base 30 is pressed forward into the rotating knob 20 to be in a locked state. After that, rotate the zeroing nut 40 in a clockwise direction until contacting and engaging the bottom gear disk 80 at the rear end of the push rod 70, and then rotating the nut fixing piece 50 to turn to make the zeroing nut 40 fixed on the zeroing nut base 30, and the zeroing step is completed. Therefore, the syringe 1 has the function of initial resetting when the injection dose is adjusted to ensure that the injection dose is adjusted more accurately.

The above are only the preferred embodiments of the present invention and do not limit the present invention in any form. Although the present invention has been disclosed as above in preferred embodiments, it is not intended to limit the present invention. Anyone familiar with the professional technology, without departing from the scope of the technical solution of the present invention, can make use of the technical content disclosed above to make slight changes or modification into equivalent embodiments with equivalent changes, but any content that does not depart from the technical solution of the present invention is based on the present invention. Any simple modifications, equivalent changes and modifications made to the above embodiments by technical essence still fall within the scope of the technical solutions of the present invention.

What is claimed is:

1. A syringe with an injection dose adjustment function, characterized in that the syringe includes a medicine vial connecting apparatus and an adjustable propulsion apparatus;

the medicine vial connecting apparatus comprises:

a housing comprising a housing base, a medicine vial assembly portion, and a joining pipe portion, the medicine vial assembly portion and the joining pipe portion respectively formed on a front end and a rear end of the housing base, the housing base having a housing middle hole extending from the front end to the rear end of the housing base, the medicine vial assembly portion having an assembly groove laterally formed in the medicine vial assembly portion and communicating with the housing middle hole;

a rotating knob unidirectionally rotatable and assembled on an outer side of the joining pipe portion of the housing, the rotating knob comprising a knob shell, a knob inner plate, a knob inner tube, and an inner hole, the knob inner plate formed in the knob shell, the knob inner tube disposed in the knob shell, the knob inner tube connected to a front end of the knob inner plate, and the inner hole disposed in the knob inner tube and the knob inner plate; and a zeroing nut base connected to a shell rear section of the rotating knob, the zeroing nut base comprising a base mount, an assembly end portion, an assembly tube portion, and a nut inner tube, the assembly end portion and the assembly tube portion respectively formed on a front end and a rear end of the base mount, and the zeroing nut base having an inner shaft hole; and the adjustable propulsion apparatus is assembled in the medicine vial connecting apparatus, and the adjustable propulsion apparatus comprises:

a screw rod comprising a screw body and a rubber stopper connecting portion formed on a front end of the screw body, the screw body having multiple screwing units formed on an outer peripheral surface of the screw body, the multiple screwing units equally spaced along an axial direction of the screw body, an annular slot formed between each two adjacent screwing units of the multiple screwing units, each screwing unit of the multiple screwing units having a spiral groove, and a front end and a rear end of the spiral groove of the each screwing unit of the multiple screwing units respectively connected to the annular slots at a front position and a rear position of the each screwing unit of the multiple screwing units; and a push assembled in the zeroing nut base, the push rod being moveable linearly relative to the zeroing nut base, the push rod being rotatable with the zeroing nut base, the push rod having a push rod hole formed in the push rod, a scale formed on an outer peripheral surface of the push rod, and a threaded portion formed on an inner wall of the push rod hole, the screw rod assembled in the push rod hole of the push rod, the threaded portion of the push rod threaded with the spiral grooves of the screw rod, the screw rod being rotatable and moveable back and forth in the push rod, the push rod having a push arm, a front end of the push arm being a free end, and the push arm extending into the annular slot of the screw rod and pressed against an end surface of the each screwing unit of the multiple screwing units.

2. The syringe with the injection dose adjustment function as claimed in claim 1, characterized in that the housing has two unidirectional snap hooks formed on an outer side of the joining pipe portion at a rear side of the housing base, the rotating knob has two unidirectional buckle grooves formed on an inner peripheral wall of a shell front section of the knob shell, and the two unidirectional snap hooks selectively and respectively engage with the two unidirectional buckle grooves.

3. The syringe with the injection dose adjustment function as claimed in claim 2, characterized in that the zeroing nut base has a guide groove portion formed on an inner wall of the inner shaft hole, the push rod has a guide rail portion formed on the outer peripheral surface of the push rod and extending axially, the guide rail portion corresponds to the guide groove portion in the zeroing nut base, the push rod is moveable linearly relative to the zeroing nut base, and the push rod is rotated together with the zeroing nut base.

4. The syringe with the injection dose adjustment function as claimed in claim 2, characterized in that the knob shell of the rotating knob has an engaging portion formed on an inner peripheral wall of the knob shell relative to a back of the knob inner plate;

the assembly end portion has a pivot annular groove and an engaging annular groove formed on an outer peripheral surface of the assembly end portion at a spaced interval, the assembly tube portion has a screw thread formed on an outer peripheral surface of the assembly tube portion, the nut inner tube is disposed in the assembly end portion and extends forward from the base mount, the nut inner tube has a second locking portion formed on a front end of the nut inner tube, the second locking portion has multiple locking recesses, the assembly end portion of the zeroing nut base is assembled in the shell rear section of the rotating knob, the engaging portion of the rotating knob is selectively engaged with the pivot annular groove or the engaging annular groove, and the second locking portion at the front end of the nut inner tube of the zeroing nut base is engaged with a first locking portion at a rear end surface of the knob inner plate of the rotating knob by concave-convex cooperation in a locked state; and the medicine vial connecting apparatus further has a zeroing nut and a nut fixing piece, wherein:

the zeroing nut has a screw hole formed in the zeroing nut, the zeroing nut has a threaded strip formed on an inner wall of the screw hole, the threaded strip has a vacant portion formed on the threaded strip, the zeroing nut has a pivot hole formed on a peripheral wall of the zeroing nut, and a position of the pivot hole corresponds to a position of the vacant portion, the zeroing nut has a first engaging segment formed on a rear end of the zeroing nut, the zeroing nut is disposed on an outer side of the assembly tube portion of the zeroing nut base, and the threaded strip is screwed to the screw thread;

the nut fixing piece includes a sheet, a pivot, and a protruding portion, the pivot is disposed on an end side of the sheet, the protruding portion is disposed on the pivot opposite to the sheet, the nut fixing piece is pivotally mounted in the pivot hole of the zeroing nut by the pivot, the sheet is located on an outer side of the zeroing nut, the protruding portion is located in the vacant portion of the threaded strip of the zeroing nut, the nut fixing piece is rotatable relative to the zeroing nut to change position relative to the vacant portion of the threaded strip; and the adjustable propulsion apparatus has a bottom gear disk disposed on a rear end of the push rod, the bottom gear disk has a second engaging segment formed on a front side of the bottom gear disk, and the second engaging segment selectively engages with the first engaging segment at the rear end of the zeroing nut.

5. The syringe with the injection dose adjustment function as claimed in claim 4, characterized in that the zeroing nut has a first positioning recess and a second positioning recess formed on the peripheral wall of the zeroing nut at two different sides relative to the pivot hole, the sheet of the nut fixing piece has a positioning flange formed on a side surface of the sheet facing the zeroing nut, and the positioning flange selectively engages with the first positioning recess and the second positioning recess with a rotation of the nut fixing piece.

6. The syringe with the injection dose adjustment function as claimed in claim 4, characterized in that the housing has an indicator mark formed on an outer peripheral surface of the housing base, the rotating knob has a marking line formed on an outer peripheral surface of the knob shell, and the marking line aligns with the indicator mark of the housing.

7. The syringe with the injection dose adjustment function as claimed in claim 4, characterized in that the zeroing nut base has a rotation indicator formed on an outer peripheral surface of the zeroing nut base to indicate a direction of rotation.

8. The syringe with the injection dose adjustment function as claimed in claim 4, characterized in that the housing has an indicator mark formed on an outer peripheral surface of the housing base, the rotating knob has a marking line formed on an outer peripheral surface of the knob shell, the marking line aligns with the indicator mark of the housing, and the zeroing nut base has a rotation indicator formed on an outer peripheral surface of the zeroing nut base to indicate a direction of rotation.

9. The syringe with the injection dose adjustment function as claimed in claim 1, characterized in that the zeroing nut base has at least one guide groove portion formed on an inner wall of the inner shaft hole, the push rod has a guide rail portion formed on the outer peripheral surface of the push rod and extending axially, the guide rail portion corresponds to the at least one guide groove portion in the zeroing nut base, the push rod is moveable linearly relative to the zeroing nut base, and the push rod is rotatable together with the zeroing nut base.

10. The syringe with the injection dose adjustment function as claimed in claim 3, characterized in that the screw rod has a stop portion formed on the screw rod between the rubber stopper connecting portion and the screw body, and the stop portion of the screw rod limits a position of the screw rod at a front end of the push rod.

11. The syringe with the injection dose adjustment function as claimed in claim 9, characterized in that the knob shell of the rotating knob has an engaging portion formed on an inner peripheral wall of the knob shell relative to a back of the knob inner plate;
the assembly end portion has a pivot annular groove and an engaging annular groove formed on an outer peripheral surface of the assembly end portion at a spaced interval, the assembly tube portion has a screw thread formed on an outer peripheral surface of the assembly tube portion, the nut inner tube is disposed in the assembly end portion and extends forward from the base mount, the nut inner tube has a second locking portion formed on a front end of the nut inner tube, the second locking portion has multiple locking recesses, the assembly end portion of the zeroing nut base is assembled in the shell rear section of the rotating knob, the engaging portion of the rotating knob is selectively engaged with the pivot annular groove or the engaging annular groove, and the second locking portion at the front end of the nut inner tube of the zeroing nut base is engaged with a first locking portion at a rear end surface of the knob inner plate of the rotating knob by concave-convex cooperation in a locked state; and
the medicine vial connecting apparatus further has a zeroing nut and a nut fixing piece, wherein:
the zeroing nut has a screw hole formed in the zeroing nut, the zeroing nut has a threaded strip formed on an inner wall of the screw hole, the threaded strip has a vacant portion formed on the threaded strip, the zeroing nut has a pivot hole formed on a peripheral wall of the zeroing nut, and a position of the pivot hole corresponds to a position of the vacant portion, the zeroing nut has a first engaging segment formed on a rear end of the zeroing nut, the zeroing nut is disposed on an outer side of the assembly tube portion of the zeroing nut base, and the threaded strip is screwed to the screw thread;
the nut fixing piece includes a sheet, a pivot, and a protruding portion, the pivot is disposed on an end side of the sheet, the protruding portion is disposed on the pivot opposite to the sheet, the nut fixing piece is pivotally mounted in the pivot hole of the zeroing nut by the pivot, the sheet is located on an outer side of the zeroing nut, the protruding portion is located in the vacant portion of the threaded strip of the zeroing nut, the nut fixing piece is rotatable relative to the zeroing nut to change position relative to the vacant portion of the threaded strip; and
the adjustable propulsion apparatus has a bottom gear disk disposed on a rear end of the push rod, the bottom gear disk has a second engaging segment formed on a front side of the bottom gear disk, and the second engaging segment selectively engages with the first engaging segment at the rear end of the zeroing nut.

12. The syringe with the injection dose adjustment function as claimed in claim 11, characterized in that the zeroing nut has a first positioning recess and a second positioning recess formed on the peripheral wall of the zeroing nut at two different sides relative to the pivot hole, the sheet of the nut fixing piece has a positioning flange formed on a side surface of the sheet facing the zeroing nut, and the positioning flange selectively engages with the first positioning recess and the second positioning recess with a rotation of the nut fixing piece.

13. The syringe with the injection dose adjustment function as claimed in claim 11, characterized in that the housing has an indicator mark formed on an outer peripheral surface of the housing base, the rotating knob has a marking line formed on an outer peripheral surface of the knob shell, and the marking line aligns with the indicator mark of the housing.

14. The syringe with the injection dose adjustment function as claimed in claim 11, characterized in that the zeroing nut base has a rotation indicator formed on an outer peripheral surface of the zeroing nut base to indicate a direction of rotation.

15. The syringe with the injection dose adjustment function as claimed in claim 11, characterized in that the housing has an indicator mark formed on an outer peripheral surface of the housing base, the rotating knob has a marking line formed on an outer peripheral surface of the knob shell, the marking line aligns with the indicator mark of the housing, and the zeroing nut base has a rotation indicator formed on an outer peripheral surface of the zeroing nut base to indicate a direction of rotation.

16. The syringe with the injection dose adjustment function as claimed in claim 1, characterized in that the knob shell of the rotating knob has an engaging portion formed on an inner peripheral wall of the knob shell relative to a back of the knob inner plate;
the assembly end portion has a pivot annular groove and an engaging annular groove formed on an outer peripheral surface of the assembly end portion at a spaced interval, the assembly tube portion has a screw thread formed on an outer peripheral surface thereof of the assembly tube portion, the nut inner tube is disposed in the assembly end portion and extends forward from the base mount, the nut inner tube has a second locking portion formed on a front end of the nut inner tube, the second locking portion has multiple locking recesses, the assembly end portion of the zeroing nut base is assembled in the shell rear section of the rotating knob, the engaging portion of the rotating knob is selectively engaged with the pivot annular groove or the engaging annular groove, and the second locking portion at the front end of the nut inner tube of the zeroing nut base is engaged with a first locking portion at a rear end surface of the knob inner plate of the rotating knob by concave-convex cooperation in a locked state; and
the medicine vial connecting apparatus further has a zeroing nut and a nut fixing piece, wherein:
the zeroing nut has a screw hole formed in the zeroing nut, the zeroing nut has a threaded strip formed on an inner wall of the screw hole, the threaded strip has a vacant portion formed on the threaded strip, the zeroing nut has a pivot hole formed on a peripheral wall of the zeroing nut, and a position of the pivot hole corresponds to a position of the vacant portion, the zeroing nut has a first engaging segment formed on a rear end of the zeroing nut, the zeroing nut is disposed on an outer side of the assembly tube portion of the zeroing nut base, and the threaded strip is screwed to the screw thread;
the nut fixing piece includes a sheet, a pivot, and a protruding portion, the pivot is disposed on an end side of the sheet, the protruding portion is disposed on the pivot opposite to the sheet, the nut fixing piece is pivotally mounted in the pivot hole of the zeroing nut by the pivot, the sheet is located on an outer side of the zeroing nut, the protruding portion is located in the vacant portion of the threaded strip of the zeroing nut, the nut fixing piece is rotatable relative to the zeroing nut to change position relative to the vacant portion of the threaded strip; and
the adjustable propulsion apparatus has a bottom gear disk disposed on a rear end of the push rod, the bottom gear disk has a second engaging segment formed on a front side of the bottom gear disk, and the second engaging segment selectively engages with the first engaging segment at the rear end of the zeroing nut.

17. The syringe with the injection dose adjustment function as claimed in claim 16, characterized in that the zeroing nut has a first positioning recess and a second positioning recess formed on the peripheral wall of the zeroing nut at two different sides relative to the pivot hole, the sheet of the nut fixing piece has a positioning flange formed on a side surface of the sheet facing the zeroing nut, and the positioning flange selectively engages with the first positioning recess and the second positioning recess with a rotation of the nut fixing piece.

18. The syringe with the injection dose adjustment function as claimed in claim 16, characterized in that the housing has an indicator mark formed on an outer peripheral surface of the housing base, the rotating knob has a marking line formed on an outer peripheral surface of the knob shell, and the marking line aligns with the indicator mark of the housing.

19. The syringe with the injection dose adjustment function as claimed in claim 16, characterized in that the zeroing nut base has a rotation indicator formed on an outer peripheral surface of the zeroing nut base to indicate a direction of rotation.

20. The syringe with the injection dose adjustment function as claimed in claim 16, characterized in that the housing has an indicator mark formed on an outer peripheral surface of the housing base, the rotating knob has a marking line formed on an outer peripheral surface of the knob shell, the marking line aligns with the indicator mark of the housing, and the zeroing nut base has a rotation indicator formed on an outer peripheral surface of the zeroing nut base to indicate a direction of rotation.

\* \* \* \* \*